US007968085B2

(12) United States Patent
Hersel et al.

(10) Patent No.: US 7,968,085 B2
(45) Date of Patent: Jun. 28, 2011

(54) HYDROGEL FORMULATIONS

(75) Inventors: Ulrich Hersel, Heidelberg/Hanschuhsheim (DE); Harald Rau, Heidelberg (DE); Robert Schnepf, Heidelberg/Dossenheim (DE); Dirk Vetter, Heidelberg/Neuenheim (DE); Thomas Wegge, Heidelberg/Ziegelhausen (DE)

(73) Assignee: Ascendis Pharma A/S (DK)

( * ) Notice: Subject to any disclaimer, the term of this patent is extended or adjusted under 35 U.S.C. 154(b) by 1348 days.

(21) Appl. No.: 10/960,851

(22) Filed: Oct. 7, 2004

(65) Prior Publication Data

US 2006/0002890 A1 Jan. 5, 2006

(30) Foreign Application Priority Data

Jul. 5, 2004 (GB) .................................. 0415041.3
Aug. 13, 2004 (EP) .................................. 04019303

(51) Int. Cl.
*A61K 31/785* (2006.01)
*A61K 31/795* (2006.01)
*A61K 38/17* (2006.01)
*A61K 48/00* (2006.01)
*A61K 38/14* (2006.01)
*A61K 31/56* (2006.01)

(52) U.S. Cl. ............ 424/78.27; 514/12; 514/34; 514/44; 514/182; 514/283; 514/49; 514/449

(58) Field of Classification Search ................ 424/78.27; 514/12, 34, 44, 182, 283, 49, 449
See application file for complete search history.

(56) References Cited

U.S. PATENT DOCUMENTS

2003/0220245 A1* 11/2003 Hubbell et al. .................. 514/12

FOREIGN PATENT DOCUMENTS

| EP | 1 053 019 B1 | 12/2003 |
|---|---|---|
| EP | 1525890 A1 | 4/2005 |
| EP | 1579873 A1 | 9/2005 |
| WO | WO 99/30727 | 6/1999 |
| WO | 9934833 A1 | 7/1999 |
| WO | 0021572 A2 | 4/2000 |
| WO | 0044808 A1 | 8/2000 |
| WO | 0185180 A1 | 11/2001 |
| WO | 02017880 A2 | 7/2002 |
| WO | 02083180 A1 | 10/2002 |
| WO | WO 02/089789 A1 | 11/2002 |
| WO | 03049677 A2 | 6/2003 |
| WO | 03101425 A2 | 12/2003 |
| WO | 2004043493 A1 | 5/2004 |

OTHER PUBLICATIONS

Na, Dong Hee, et al., *J. Contr. Rel.*, vol. 92, 291-299, (2003).
Hennink, W.E. et al., *Adv. Drug Del. Rev.*, vol. 54, 13-36, (2002).
Hoffman, A.S., *Adv. Drug Del. Rev.*, vol. 43, 3-12, (2002).
Caliceti, P. et al., *Adv. Drug Del. Rev.*, vol. 55, 1261-1277, (2003).
Duncan, R., et al., *J. Contr. Rel.*, vol. 74, 135-146, (2001).
Cadee, J.A., et al., *J. Contr. Rel.*, vol. 78, 1-13, (2002).
Wiwattanapatapee, W.R., et al., *J. Contr. Rel.*, vol. 88, 1-9, (2003).
Surini, S., et al., *J. Control. Rel.*, vol. 90, 291-301, (2003).
Luo, Y., et al., "A Hyaluronic Acid—Taxol Antitumor Bioconjugate Targeted to Cancer Cells," *Biomacromolecules*, vol. 1, 208-218, (2000).
Jeong, B., et al., "Thermogelling Biodegradable Copolymer Aqueous Solutions for Injectable Protein Delivery and Tissue Engineering," *Biomacromolecules*, vol. 3, 865-868, (2002).
Sawhney, A.S., et al., "Bioerodible Hydrogels Based on Photopolymerized Poly(ethylene glycol)-co-poly($\alpha$-hydroxy acid) Diacrylate Macromer," *Macromolecules*, vol. 26, 581-587, (1993).
Cheng, J., et al., "Synthesis of Linear, Beta-Cyclodextrin Based Polymers and Their Camptothecin Conjugates," *Bioconjugate Chem.*, vol. 14, 1007-1017, (2003).
Satchi-Fainaro, R., et al., *Bioconjugate Chem.*, vol. 14, 797-804, (2003).
Cavallaro, G., et al., *Bioconjugate Chem.*, vol. 12, 143-151, (2001).
Lee, S., et al., *Bioconugate. Chem.*, vol. 12(2), 163-169, (2001).
Greenwald, R.B., et al., *J. Med. Chem.*, vol. 47, 726-734, (2004).
Bhatt, R., et al., "Synthesis and In Vivo Antitumor Activity of Poly(L-glutamic acid) Conjugates of 20(S)-Campthecin," *J. Med. Chem.*, vol. 46, 190-193, (2003).
Greenwald, R.B., et al., *J. Med. Chem.*, vol. 43(3), 457-487, (2000).
Greenwald, R.B., et al., *J. Med. Chem.*, vol. 42, 3657-3667, (1999).
Garman, A.J., et al., *FEBS Lett.*, vol. 223(2), 361-365, (1987).
Nektar, Inc., "Nektar Molecule Engineering—Polyethylene Glycol and Derivatives for Advanced PEGylation," (2003).
Antczak, et al., *Bioorg. & Med. Chem.*, vol. 9, 2843-2848, (2001).
Peppas, N.A., et al., "Hydrogels in Pharmaceutical Formulations," *Eur. J. Pharm. & Biopharm.*, vol. 50, 27-46, (2000).
Esfand, R., et al., *Drug Discov. Today*, vol. 6(8), 427-436, (2001).
Boas, U., et al., *Chem. Soc. Rev.*, vol. 33(1), 43-63, (2004).
Grayson, S.M., et al., *Chem. Rev.*, vol. 101(12), 3819-3868, (2001).
Yasuhiro Matsumura, et al., "A New Concept for Macromolecular Therapeutics in Cancer Chemotherapy: Mechanism of Tumoritropic Accumulation of Proteins and the Antitumor Agent Smancs", Cancer Research 46, 6387-6392, (Dec. 1986).
Theodora Greene, et al., "Protective Groups in Organic Synthesis" Third Edition (1998).
Bernard Testa, et al., "Hydrolysis in Drug and Prodrug Metabolism/ Chemistry, Biochemistry and Enzymology", (2002).

(Continued)

*Primary Examiner* — James D Anderson
*Assistant Examiner* — Zohreh Vakili
(74) *Attorney, Agent, or Firm* — Kelly K. Reynolds; Steven J. Hultquist; Hultquist IP

(57) ABSTRACT

A polymeric prodrug composition including a hydrogel, a biologically active moiety and a reversible prodrug linker. The prodrug linker covalently links the hydrogel and the biologically active moiety at a position and the hydrogel has a plurality of pores with openings on its surface. The diameter of the pores is larger than that of the biologically active moiety at least at all points of the pore between at least one of the openings and the position of the biologically active moiety.

16 Claims, 10 Drawing Sheets

OTHER PUBLICATIONS

Auzanneau, F. et al. , "Synthesis, characterization, and biocompatability of PEGA resins", "Journal of Peptide Science", May 1995, pp. 31-44, vol. 1.

Franssen, O. et al. , "Controlled release of a model protein from enzymatically degrading dextran micospheres ", "Journal of Controlled Release", May 1999, pp. 219-228, vol. 59, No. 2.

Prestwich, G.D. et al. , "Controlled chemical modification of hyalonuric acid: synthesis, applications, and biodegradation of hydrazide derivative", Apr. 30, 1998, pp. 93-103, vol. 53, No. 1-3.

Rouquerol J. et al. , "Recommendations for the characterization of porous solids", "Pure and Applied Chemistry", 1994, pp. 1739-1758, vol. 66, No. 8.

* cited by examiner (same symbols used as in figure 2)

Insulin release from polyacrylamide-based mesoporous hydrogel prodrug 4

Insulin release from carbohydrate-based mesoporous hydrogel prodrug 16

In vivo rh-insulin release from polyacrylamide-based mesoporous hydrogel prodrug 4 and 5a Insulin release from biodegradable polyacrylamide based mesoporous hydrogel prodrug 11

LCMS characterization of hydrogel-bound rh-insulin integrity upon in vivo incubation for 6 days Degradation of biodegradable hydrogel 20 (4 cross-links) and 21 (8 cross-links)

HYDROGEL FORMULATIONS

FIELD

The present invention is directed to hydrogel depot formulations of biologically active moieties. The hydrogel depot formulations comprise biologically active moieties such as peptides, proteins, oligonucleotides or polynucleotides, natural products or synthetic chemical compounds linked reversibly to mesoporous hydrogels.

BACKGROUND OF THE INVENTION

Definitions

Micropore:
Pore in a three-dimensional polymer network that is smaller than a given biologically active moiety (smaller than 1 nanometer (nm))

Mesopore:
Pore in a three-dimensional polymer network that is larger than a given biologically active moiety (dependent upon the size of the biologically active moiety, but usually larger than 1 nm, and smaller than 100 nm)

Macromonomer:
A polymer or oligomer whose molecules each have at least one polymerizable functional group, often at the end or at the ends, that enables it to act as a monomer. After polymerization, the groups are part of the main chain of the final polymer. Homopolymerization or copolymerization of a macromonomer yields comb, graft, or cross-linked polymers.

Crosslinking:
A reaction involving pairs of polymer chains that results in the formation of regions in a polymer from which at least four chains emanate. The region may be an atom, a group of atoms, or a number of branch points connected by bonds, groups of atoms, oligomeric, or polymeric chains.

Biodegradable Polymer:
A polymer susceptible to degradation under in vivo conditions. In vivo conditions include, but are not limited to, degradation by enzymatic or chemical means under conditions present in a living body. Degradation is defined as a chemical change in a polymeric material, accompanied by cleavage of chemical bonds in the polymer and a lowering of its molar mass.

Reactive Polymer:
A polymer having reactive functional groups that can be transformed under the conditions required for a given reaction or application.

Hydrogel:
A hydrogel may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm.

Prodrug:
A prodrug is any compound that undergoes biotransformation before exhibiting its pharmacological effects. Prodrugs can thus be viewed as biologically active moieties (such as drugs) containing specialized non-toxic protective groups used in a transient manner to alter or to eliminate undesirable properties in the parent molecule.

Carrier-Linked Prodrug (Carrier Prodrug):
A carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

Cascade Prodrug:
A cascade prodrug is a prodrug for which the cleavage of the carrier group becomes effective only after unmasking an activating group.

Protein Depots

Among the first polymers employed for protein drug delivery applications were polylactide-coglycolides (PLGA). These materials are rather hydrophobic, and only few protein and peptide drugs could be formulated into delivery systems (e.g., somatropin, Nutropin Depot; triptorelin, Trelstar™ Depot; octreotide, Sandostatin® LAR®; leuprolide, Lupron Depot®). The hydrophobic nature of PLGA is exploited in the production process of such PLGA-protein formulations. PLGA is provided as a solution in a water-miscible organic solvent, protein is dissolved in water, and the two solutions are mixed in a mixing step. As a consequence, PLG precipitates and physically entraps the protein in a precipitate. The precipitate has a low water content, and pore sizes are smaller than 1 nm and do not exhibit hydrogel-like properties. Dependent on the conditions of the mixing step, the water-miscible organic solvent used and the physicochemical properties of the protein, the loading of the precipitate of the PLGA and the protein may vary greatly.

Furthermore, Dong Hee Na, et al. showed that upon degradation of the precipitates the encapsulated protein and peptide drugs are chemically modified by acylation resulting in the release of modified drug moieties (see Dong Hee Na, et al., 2003, J. Contr. Release 92, 291-299).

In order to address a fundamental shortcoming of PLGA-precipitates, recent developments focused on the use of hydrogels for protein delivery. Hydrogels are promising materials for drug delivery applications, in particular for the delivery of peptide, protein, oligonucleotide or polynucleotide drugs ("biotherapeutics"). These biotherapeutics are fragile macromolecules which often require a well-hydrated environment for activity and structural integrity. The high water content of the hydrogels renders the material biocompatible and minimizes inflammation reactions of tissue in contact with the hydrogel. Especially for the delivery of protein therapeutics, the high degree of hydration may help to preserve the folding of the protein which is a prerequisite for its bioactivity. In hydrophobic environments, proteins tend to denature and aggregate and lose activity.

Two different approaches for the preparation of hydrogel-based depots are known in the art, non-covalent depots and covalent depots.

In the non-covalent approach, biologically active moieties such as drugs are encapsulated physically without chemical linkage to the hydrogel. For this approach, the average pore size in the three-dimensional network of the hydrogel has to be smaller than the size of the biologically active moiety for efficient encapsulation by the hydrogel. Therefore, the biologically active moiety can not be incorporated into the hydrogel after hydrogel formation. In the non-covalent approach, the hydrogels have to be chemically crosslinked in the presence of the biologically active moiety or pores have to be formed through physical crosslinks in a self-assembly process, also in the presence of the biologically active moiety. The size of the pore size is the key factor governing the encapsulation of the biologically active moiety. If the pores are larger than the biologically active moiety, then the biologically active moiety will rapidly effuse out of the interior of the hydrogel (so-called "burst" release). Therefore the crosslinking is allowed to proceed to such extent that a hydrogel with pores is formed, and the biologically active moiety is physically entrapped inside the pores.

The size of the pore in a chemically crosslinked hydrogel may be determined by the measurement of the diffusion of different molecules with known sizes (for example a set of different proteins) into the hydrogels. For example, this can be done experimentally by size exclusion chromatography in which the hydrogel is shaped in bead form and packed into a size exclusion chromatography column. Once the hydrodynamic diameter of the protein is larger than the pores in the hydrogel, no diffusion of the protein into the beads made of the hydrogel can take place and the protein elutes in the exclusion volume of the exclusion chromatography column.

The size of the pores in self-assembled networks is difficult to measure due to the structural instability of self-assembled networks, which is due to the usually weak physical interactions within the self-assembled network.

The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose. (see.: W. E. Hennink and C. F. van Nostrum, Adv. Drug Del. Rev. 2002, 54, 13-36 and A. S. Hoffman, Adv. Drug Del. Rev. 2002, 43, 3-12). These materials consist of high-molecular weight backbone chains made of linear or branched polysaccharides or polypeptides.

Examples for drug-biopolymer hydrogel encapsulation include the encapsulation of recombinant human interleukin-2 from in chemically crosslinked dextran-based hydrogels (J. A. Cadee et al., J Control. Release. 2002, 78, 1-13) and the encapsulation of insulin in an ionically chrosslinked chitosan/hyaluronan complex (S. Surini et al., J. Control. Release 2003, 90, 291-301)

Examples of hydrogels based on chemical or physical crosslinking synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, Adv. Drug Del. Rev 2002, 43, 3-12).

Examples for protein-polymer encapsulation include the encapsulation of insulin in physically crosslinked PEG-g-PLGA and PLGA-g-PEG copolymers (see B. Jeong et al. Biomacromolecules 2002, 3, 865-868) and the encapsulation of bovine serum albumin in chemically crosslinked acrylate-PGA-PEO-PGA-acrylate macromonomers (see A. S. Sawhney et al., Macromolecules, 1993, 26, 581-587)

This first non-covalent approach has several drawbacks. As the polymerization or crosslinking step to form the hydrogel has to be carried out in the presence of the biologically active moiety (i.e. a protein), the biologically active moiety is exposed to solvents and polymerization reaction conditions which may cause denaturation or chemical modification of the biologically active moiety. Furthermore, the quality of the end product is difficult to control and batch to batch variations may occur. Additionally, the loading of the hydrogels with the biologically active moiety is usually rather low (<15% protein) and is difficult to control.

A further drawback of the non-covalent type of the hydrogels is the so-called burst effect. The burst effect is characterized by a fast and uncontrolled initial release of a weakly-bound biologically active moiety from the hydrogel. The initial burst release can account for up to 20% of the encapsulated biologically active moiety.

As in PLGA precipitates, degradation of the hydrogels is required for release of the biologically active moiety from the crosslinked hydrogels. Self-assembled systems may also depend on degradation or disaggregation for release of the biologically active moiety. Degradation of the hydrogel increases the size of the pore to the extent that the biologically active moiety may diffuse out of the interior of the hydrogel into surrounding body fluids to exert its bioactivity. Degradation of the hydrogel is a process which is dependent on a number of parameters, some of which are not well understood. As the degradation of the hydrogel is dependent upon in vivo conditions, there may be significant contribution of complex biodegradation processes to the overall degradation of the hydrogel.

The small size of the pore may reduce the water content of the hydrogel and therefore its compatibility with fragile biomolecules.

It is difficult to optimize release kinetics in vivo, which depend in turn on the conditions of the copolymerization process carried out in presence of the biologically active moiety. This poses altogether a significant obstacle for the successful development of these types of drug delivery systems.

Other inherent drawbacks of degradation-dependent release of the biologically active moiety are interpatient and injection site variability when the degradation is catalyzed by enzymes. Enzyme levels and specificities vary greatly between patients and also in dependence on the tissue chosen for injection and other difficult-to-control parameters such as the depth of needle insertion. Furthermore, lack of control over degradation typically may lead to burst effects.

Another complication lies in the fact that polymer degradation under in vivo conditions may also occur chemically, without the contribution of biological factors such as enzymes. For instance, ester bonds typically employed as biodegradable bonds (cleavable by esterases but also certain proteases) may spontaneously hydrolyze at the biological pH of 7.4 in plain buffer in the absence of ester-cleaving proteins. Typically, microporous hydrogels require a high amount of ester bonds in order to effect efficient release of the biologically active moiety. Both the high local concentration of the ester bonds and the tight encapsulation of the biologically active moiety may lead to side reactions. It may be possible that an amino group present in the biologically active moiety may be positioned in proximity to an ester group, with the amino group providing a nucleophile effecting ester cleavage and subsequent amidation. This process results in a very stable amide linkage between the biologically active moiety and the polymer. The biologically active moiety will not be released until the polymer chain to which the biologically active moiety is attached, is degraded, and the biologically active moiety will be permanently modified. Such modifications are known to reduce bioactivity of the biologically active moiety and may also cause side effects, such as immunogenicity or carcinogenicity. In addition, this undesirable modification process is largely uncontrolled and gives rise to a variety of molecular species. This type of side-reaction is described in Dong Hee Na et al., 2003, J. Contr. Release 92, 291-299.

In the alternative covalent depot approach, the biologically active moiety (such as a drug molecule) is reversibly attached to the hydrogel by a covalent or ionic linkage. In this case a hydrogel with mesopores (a so-called mesoporic hydrogel) can be used. The release of the biologically active moiety from the mesopores in the hydrogels is prevented by the attachment of the biologically active moiety.

There are only few examples describing this second approach of reversibly linking the biologically active moiety to the hydrogel.

J. Harris and X. Zhao (in European Patent No. EP 1 053 019 B1) describe the reversible covalent attachment of a lysozyme protein to a hydrogel prepared by radical copolymerization of a PEO-diacrylate and a lysozyme-modified PEO-monoacrylate. The lysozyme was coupled to the PEO-monoacrylate via a thiourea group and a short biodegradable ester linker. Release of the lysozyme from the hydrogel was effected by incubation in pH 7 buffer.

Upon cleavage of the ester bond in the approach described in the '019 patent application, modified protein moieties are released as the cleaved linker moiety is still attached to the protein via the stable thiourea group. Furthermore, as the reaction of the activated linker-PEO-monoacrylate with the amino groups of the lysozyme is not regioselective, a variety of differently modified regioisomers are released, which is undesirable. Furthermore, as the encapsulation of the protein is upon hydrogel formation by radical polymerization, the protein can, in addition to the covalent attachment, also be encapsulated in pores of the formed three-dimensional network that are smaller than the diameter of the protein. Therefore, the release of the protein is not solely governed by cleavage of the linker but can also be influenced by the structure of the hydrogel.

Hubbell and coworkers (U.S. Patent Application Publication No. 2003/0220245 A1) described in a similar approach the reversible attachment of a small synthetic peptide via a cysteine residue to a non-biodegradable hydrogel. The peptide was coupled to PEO-diacrylate by a Michael addition reaction. The peptide modified PEO-monoacrylate was radically crosslinked with a PEG-diacrylamide to form a peptide modified hydrogel. Release of the propionyl-modified peptide was effected by incubation of the hydrogel in pH 7.4 buffer at 37° C.

Due to the current use of microporous hydrogel materials in both non-covalent and covalent drug depots, numerous problems have hindered the development of a robust and reliable system for sustained drug delivery from a depot formed from a hydrogel.

DETAILED DESCRIPTION OF THE INVENTION

It has now been surprisingly discovered that mesoporous hydrogels can be used as polymer carriers for drug depots if provided as a carrier in a prodrug system.

The invention is directed towards mesoporous hydrogel prodrugs (MHP) of biologically active moieties, such as drug molecules. The MHP may be administered to a patient to form a depot inside the patient which provides for a sustained release of the biologically active moiety over a desired period of time.

A main advantage of the MHPs is to provide depot formulations without the need for encapsulation. Until now, many biocompatible hydrogel materials with large pore sizes could not be used for drug formulation due to their lack of encapsulating properties. In such biocompatible hydrogel materials, biologically active moiety would be released too fast for most therapeutic applications from such well-hydrated and mechanically soft materials. The provision of a hydrogel as a prodrug carrier according to the invention allows the development of superior drug delivery systems. Carrier material properties such as biocompatibility (minimal irritation, immunogenicity, toxicity) may be optimized independently from the release properties of the biologically active moiety as the release properties are solely governed by the prodrug linker cleavage kinetics. The release of the biologically active moiety is therefore largely independent from the carrier material (i.e., the hydrogel) and does not require chemical or enzymatic degradation of the hydrogel.

The MHP system consists of three parts, a mesoporous hydrogel carrier, a prodrug linker and a biologically active moiety, such as a drug molecule. The prodrug linker is covalently bonded to the mesoporous hydrogel carrier and to the biologically active moiety in such a fashion that the biologically active moiety-linker-hydrogel conjugate is a carrier prodrug.

Biologically Active Moiety

Suitable biologically active moieties include, but are not limited to, small organic molecule bioactive agents, biopolymers like proteins, polypeptides and oligo- or poly-nucleotides (RNA, DNA), and peptide nucleic acids (PNA).

Suitable organic small molecule bioactive drugs include, without limitation, moieties such as central nervous system-active agents, anti-infective agents, anti-neoplastic agents, antibacterial agents, anti-fungal agents, analgesic agents, contraceptive agents, anti-inflammatory agents, steroidal agents, vasodilating agents, vasoconstricting agents, and cardiovascular agents. Non-exclusive examples of such compounds are daunorubicin, doxorubicin, idarubicin, mitoxantron, aminoglutethimide, amantadine, diaphenylsulfon, ethambutol, sulfadiazin, sulfamerazin, sulfamethoxazol, sulfalen, clinafloxacin, paclitaxel, moxifloxacin, ciprofloxaxin, enoxacin, norfloxacin, neomycin B, sprectinomycin, kanamycin A, meropenem, dopamin, dobutamin, lisinopril, serotonin, carbutamid, acivicin, etc.

Suitable proteins and polypeptides include, but are not limited to, ACTH, adenosine deaminase, agalsidase, albumin, alfa-1 antitrypsin (AAT), alfa-1 proteinase inhibitor (API), alteplase, anistreplase, ancrod serine protease, antibodies (monoclonal or polyclonal, and fragments or fusions), antithrombin III, antitrypsins, aprotinin, asparaginases, biphalin, bone-morphogenic proteins, calcitonin (salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucocerebrosidase, granulocyte macrophage colony stimulating factor (GM-CSF), phospholipase-activating protein (PLAP), gonadotropin chorionic (hCG), hemoglobins, hepatitis B vaccines, hirudin, hyaluronidases, idumonidase, immune globulins, influenza vaccines, interleukins (1 alfa, 1 beta, 2, 3, 4, 6, 10, 11, 12), IL-1 receptor antagonist (rhIL-1ra), insulins, interferons (alfa 2a, alfa 2b, alfa 2c, beta 1a, beta 1b, gamma 1a, gamma 1b), keratinocyte growth factor (KGF), transforming growth factors, lactase, leuprolide, levothyroxine, luteinizing hormone, lyme vaccine, natriuretic peptide, pancrelipase, papain, parathyroid hormone, PDGF, pepsin, platelet activating factor acetylhydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urate oxidase, urokinase, vaccines, and plant proteins such as lectins and ricins.

Also included herein is any synthetic polypeptide or any portion of a polypeptide with in vivo bioactivity. Furthermore, proteins prepared by recombinant DNA methodologies including mutant versions of aforementioned proteins, antibody fragments, single chain binding proteins, catalytic antibodies and fusion proteins are included.

Linker

It is preferred for the linking agent to form a reversible linkage to the biologically active moiety, preferably in such a fashion that after cleavage of the linker, the biologically active moiety is released in an unmodified form. A variety of different linking agents or linking groups may be applied for this purpose; see B. Testa et al. (B. Testa, J. Mayer, Hydrolysis in Drug and Prodrug Metabolism, Wiley-VCH, 2003).

In a preferred embodiment, the linker is a cascade prodrug linker constituted of a masking group and an activating group. The biologically active moiety is bound to the activating group, preferably through a carbamate bond. The release of the biologically active moiety is effected by a two-step mechanism. In the first step, the masking group is detached from the linker by cleavage of the bond connecting the masking group and activating group. The bond connecting the masking group and the activating group may also be a carbamate bond.

Subsequently, in a second step, the bond between biologically active moiety and the activating group is cleaved, and the biologically active moiety is released. As this second step is faster than the first step, the cleavage of the masking group is the rate-limiting step of the release of the biologically active moiety.

The cleavage of the masking group is preferably based on a hydrolytic process, most preferably catalyzed by a nucleophile present in the masking group. In an autocatalytic fashion, this nucleophile attacks in an intramolecular fashion the carbon of the carbamate group constituting the linkage between the masking group and the activating group. The presence of the nucleophile in the vicinity of the carbamate group enhances the susceptibility of the carbamate group to hydrolysis. In a preferred embodiment, the nucleophile is a tertiary amine which does not undergo a reaction with the carbamate carbonyl and does not lead to a cyclization product.

Release of the biologically active moiety is initiated by an intramolecular rearrangement of the 1,6-elimination type, followed by autohydrolysis.

It is also preferred that at least part of the linker remains attached to the hydrogel after cleavage of the bond with the biologically active moiety. If the linker is a cascade prodrug linker, it is preferred for the activating group to remain stably bound to the hydrogel.

Reactive Mesoporous Hydrogel

Hydrogels are three-dimensional, hydrophilic or amphiphilic polymeric networks capable of taking up large quantities of water. The networks are composed of homopolymers or copolymers and are insoluble due to the presence of covalent chemical or physical (ionic, hydrophobic interactions, entanglements) crosslinks. The crosslinks provide the network with structure and physical integrity.

Such reactive mesoporous hydrogels are characterized by the following structural components: crosslinking moiety, backbone moiety, reactive functional groups, pores, and optionally biodegradable bonds.

Backbone and Crosslinking Moieties

Non-limiting examples for suitable polymers for the synthesis of hydrogels are chemically or physically crosslinked functionalized or non-functionalized polyalkyloxy-based polymers like poly(propylene glycol) or poly(ethylene glycol), dextran, chitosan, hyaluronic acid and derivatives, alginate, xylan, mannan, carrageenan, agarose, cellulose, starch, hydroxyethyl starch (HES) and other carbohydrate-based polmers, poly(vinyl alcohols), poly(oxazolines), poly(anhydrides), poly(ortho esters), poly(carbonates), poly(urethanes), poly(acrylic acids), poly(acrylamides) such as poly(hydroxypropylmethacrylamide) (HMPA), poly(acrylates), poly(methacrylates) like poly(hydroxyethylmethacrylate), poly(organophosphazenes), poly(siloxanes), poly(vinylpyrrolidone), poly(cyanoacrylates), poly(esters) such as poly (lactic acid) or poly(glycolic acids), poly(iminocarbonates), poly(amino acids) such as poly(glutamic acid) or polylysine, collagen, gelatin, copolymers, grafted copolymers, crosslinked polymers, hydrogels, and block copolymers from the above listed polymers.

These polymers may serve as backbone moieties or crosslinking moieties. In addition to oligomeric or polymeric crosslinking moieties, low-molecular crosslinking moieties may be used, especially when hydrophilic high-molecular weight backbone moieties are used for the hydrogel formation.

Suitable physical or chemical crosslinking methods are known to the person skilled in the art and are described in W. E. Hennink and C. F. van Nostrum, Adv. Drug Del. Rev. 2002, 54, 13-36.

Pores

The chains of the network in a mesoporous hydrogel are connected in such a fashion that pores exist in the hydrated state and that a substantial fraction of these pores are of dimensions between 1 and 100 nm.

The hydrogel is mesoporous with respect to the biologically active moiety (e.g. drug molecule) to be carried, i.e. the average size of the pore of the hydrogel is larger than the diameter of the biologically active moiety. For instance, a hydrogel that is mesoporous with respect to insulin molecules has pores of more than 4 nm in size (in the hydrated state).

The dimensions of the pores may be controlled by adjusting both length of crosslinker and degree of crosslinking.

For example, if small molecule crosslinkers are used for instance on a biopolymer such as dextran, porosity may be controlled through the degree of crosslinking. Usually, the lower the degree of crosslinking is the larger the size of the pores.

The size of the pore increases with crosslinker length. Crosslinker length refers to the spacer length between the two reactive groups used for the crosslinking of the backbone moiety. A typical polymeric crosslinker for the mesoporous hydrogel has at least two functional groups, usually at the ends of the polymeric chain. The functional groups are usually connected by a linear or branched chain of MW between 500 and 50000. Such crosslinkers may be macromonomers, in which case the macromonomers are characterized by having at least two polymerizable functional groups.

Functional Groups

The hydrogel is a functionalized material. The reactive functional groups serve as conjugation sites for the linker. Ideally, the reactive functional groups are dispersed homogeneously throughout the hydrogel, and may or may not be present on the surface of the hydrogel. Non-limiting examples of such reactive functional groups include but are not limited to carboxylic acid and activated derivatives, amino, maleimide, thiol, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, epoxide, oxirane, and aziridine.

Preferred functional groups for the polymer include, but are not limited to, thiol, maleimide, amino, carboxylic acid and derivatives, carbonate and derivatives, carbamate and derivatives, aldehyde, and haloacetyl.

In a preferred embodiment of the invention, the reactive mesoporous hydrogel is in the form of a shaped article such as a mesh or a stent. Most preferably, the hydrogel is formed into microparticulate beads that can be administered as subcutaneous or intramuscular injectably by means of a standard syringe. Such soft beads may have a diameter of between 1 and 500 micrometers.

Biodegradable Bonds

Biodegradability of the mesoporous hydrogel is of importance if the hydrogel is to be used for medical applications such as wound healing, wound sealing or for drug delivery (or, indeed, delivery of any type of biologically active moieties). In such applications, the hydrogel is administered by a subcutaneous or intramuscular injection or applied topically to a wound and left in the organism to be degraded in vivo and resorbed or excreted.

For biodegradability of the hydrogel, biodegradable bonds have to be incorporated into the backbone and/or crosslinking moieties. The susceptibility of these biodegradable bonds to cleavage under in vivo conditions may cause complete degradation of the hydrogel after a certain time period, which is desirable for the abovementioned applications in the medical field. Cleavage of these biodegradable bonds may be enzymatically or chemically triggered, or be a combination of both.

Biodegradable bonds which may be cleaved chemically under in vivo conditions include, but are not limited to, phosphate, phosphonate, carbonate, carbamate, disulfide and ester bonds.

There exists a huge variety of bonds that may be cleaved enzymatically. Hydrogels with biopolymer backbones or biopolymer crosslinkers are per se biodegradable on the surface of the hydrogel article if enzymes are present for which the backbone chains are substrates. The rate of degradation under in vivo conditions is different for every different type of hydrogel. In general, the degradation rate is a function of the degradability of the backbone (number of cleavable bonds, dependence of bond cleavage on autohydrolysis or enzymatic catalysis) and the degree of crosslinking. Even though crosslinks do not directly contribute to the degradability of the hydrogel, the crosslinks can enable enzyme access into the hydrogel if the degree of crosslinking is small enough that the pores are large enough for the enzymes to penetrate into the hydrogel. Suitable biopolymers include, but are not limited to, carbohydrate-based polymers like dextran, chitosan, hyaluronic acid and derivatives, alginate, xylan, mannan, carrageenan, agarose, cellulose, starch, and hydroxyethyl starch and poly- or oligopeptide based oligomers or polymers like synthetic peptide sequences, collagen and gelatin.

MHP Preparation Process

In order to guarantee that the prodrug of the biologically active moiety is only coupled to mesopores of the hydrogel, the biologically active moiety has to be reacted with the hydrogel after the hydrogel has been synthesized. This ensures that the release of the biologically active moiety from the hydrogel is governed by the prodrug linker and is independent from the optional hydrogel degradation. This is because after cleavage of the prodrug linker the biologically active moiety can freely diffuse out of the mesopores of the hydrogel.

A further advantage of this method of preparation is that reagents and solvents contacted with the hydrogel during the preparation of the hydrogel may be removed from the hydrogel after completion of the preparation by a filtration step. Efficient reagent and solvent removal avoid denaturation or modification of the biologically active moiety added to the hydrogel. Efficient reagent and solvent removal also avoids leakage of potentially toxic substances after administration to an organism.

Representative examples for the preparation of MHP are given in the exapmples section. MHPs can also be prepared by several other methods.

To prepare a MHP (Method A in FIG. 1), a prodrug linker agent can be coupled to the reactive mesoporous hydrogel in a first reaction step. Such a suitable prodrug linking agent carries two functional groups. The first one of the functional groups would serve as the attachment of the prodrug linker to the hydrogel, and the second one of the functional groups would subsequently be conjugated to the biologically active moiety through a suitable functional group present in the biologically active moiety.

Such first reactive functional groups should be complementary to a functional group present in the reactive mesoporous hydrogel. Non-limiting examples of such first reactive functional groups include, but are not limited to, carboxylic acid and activated derivatives, amino, maleimide, thiol, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated Michael acceptors, arylating agents like aryl fluorides, hydroxylamine, disulfides like pyridyl disulfide, vinyl sulfone, vinyl ketone, diazoalkanes, diazoacetyl compounds, epoxide, oxirane, and aziridine.

Preferred first functional groups of the prodrug linker include thiol, maleimide, amino, carboxylic acid and derivatives, carbonate and derivatives, carbamate and derivatives, aldehyde, and haloacetyl.

After activation of the second one of the functional groups of the prodrug linker, the linker-hydrogel conjugate may be contacted with the biologically active moiety in the second reaction step and excess biologically active moiety (e.g., excess drug) may be removed by filtration after conjugation of the biologically active moiety to the hydrogel-bound prodrug linker. Despite the large size of the pore of the hydrogel, the biologically active moiety remains bound inside the hydrogel by the covalent attachment of a suitable functional group present on the biologically active moiety to the second functional group of the prodrug linker.

Suitable second functional groups of the prodrug linker include, but are not limited to, carboxylic acid and derivatives, carbonate and derivatives, hydroxyl, hydrazine, hydroxylamine, maleamic acid and derivatives, ketone, amino, aldehyde, thiol and disulfide.

Suitable functional groups present on the biologically active moiety include, but are not limited to, thiol, carboxylic acid, amino, hydroxyl, ketone, and imidazole.

Optionally this reaction sequence may be inverted, and the prodrug linker may be first conjugated to the biologically active moiety and the resulting biologically active moiety—prodrug linker conjugate may then react with the reactive mesoporous hydrogel (Method B in FIG. 1).

These preparation methods are shown schematically in FIG. 1.

Reactive Mesoporous Hydrogel Synthesis Process

Hydrogels which are reactive and mesoporous may be prepared by a variety of different methods. One particular synthesis process is based on using a crosslinking macromonomer carrying at least two polymerizable functional groups and a non-crosslinking macromonomer or monomer carrying one polymerizable functional group and at least one functional group that is not intended to participate in the polymerization step. Additional diluent monomers may or may not be present. Copolymerization of these components results in a hydrogel containing functional groups provided by the non-crosslinking macromonomer. In order to ensure that the functional group is available for reactions after completion of the polymerization, the conditions for polymerization are chosen such that the functional group is not modified. Alternatively, the functional group may be protected by use of a reversible protecting group known to the person skilled in the art, which is removed after the polymerization.

Useful polymerizable functional groups include, but are not limited to, radically polymerizable groups like vinyl, vinyl-benzene, acrylate, acrylamide, methacylate, methacrylamide and ionically polymerizable groups like oxetane, aziridine, and oxirane.

In an alternative method of preparation, the hydrogel is generated through chemical ligation reactions. The hydrogel may be formed from two macromolecular educts with complementary functionalities which undergo a reaction such as a condensation or addition. One of these starting materials is a crosslinker with at least two identical functional groups and the other starting material is a homomultifunctional backbone structure. Suitable functional groups present on the crosslinker include terminal amino, carboxylic acid and derivatives, maleimide and other alpha,beta unsaturated Michael acceptors like vinylsulfone, thiol, and hydroxyl groups. Suitable functional groups present in the backbone structure include, but are not limited to, amino, carboxylic acid and derivatives, maleimide and other alpha,beta unsaturated Michael acceptors like vinylsulfone, thiol, and hydroxyl groups.

If the crosslinker reactive functional groups are used substoichiometrically with respect to backbone reactive functional groups, the resulting hydrogel will be a reactive hydrogel with free reactive functional groups attached to the backbone structure.

MHP with Staged Release and Degradation Kinetics

This invention also includes degradable mesoporous hydrogel prodrugs exhibiting minimal release of biologically active moiety conjugated to hydrogel degradation products.

In general, it is of advantage to limit the structural diversity of degradation products of a polymeric drug formulation with respect to chain lengths, substitutions or modifications. Specifically, the release of biologically active moiety-polymer conjugates should be avoided. Hydrogel degradation may result in the release of degradation product conjugates of the biologically active moiety tethered to degradation products by means of the prodrug linker if degradation kinetics of the hydrogel are of a similar order as prodrug cleavage kinetics. The degradation product conjugates (shown schematically in FIG. 4) are undesired modifications of the biologically active moieties. Only few of these degradation product conjugates will appear if the cleavage of degradable hydrogel is at least one order of magnitude slower than the release of the biologically active moiety. There may, however, be applications, such as weekly injections of MHP in which a more rapid disintegration of the hydrogel is desirable.

It has now been surprisingly found that through controlling the degree of crosslinking, the degree of chain length of the backbone polymer, the positioning of degradable bonds and the site of the prodrug linker, the release kinetics of the resulting degradation products from the hydrogel can be fine-tuned and the heterogeneity of degradation products can be minimized.

In such a hydrogel with controlled degradation properties, the degradable bonds are exclusively located in the crosslinking chains. In a most preferred embodiment, there are precisely two degradable bonds per linear crosslinking chain and they are positioned between the chain and backbone attachment site. The crosslinker carrying the degradable bonds is symmetrical with respect to the degradable bonds, rendering the bonds chemically identical. Such a biodegradable mesoporous hydrogel prodrug is shown schematically in FIG. 2.

Functional groups for attachment of the prodrug linker are positioned on side chains emanating from the backbone polymer. There are no degradable bonds between these functional groups and the non-biodegradable backbone or in the non-biodegradable backbone itself.

Cleavage of the degradable bonds of the crosslinker results in a two-stage process. Shortly after initial time only cleavage products containing crosslinker units are released from the hydrogel when each non-biodegradable backbone is linked with at least one other non-biodegradable backbone via several crosslinkers. If, for instance, esters of PEG have been used, the released compound is PEG. The release of PEG from this type of hydrogel follows approximately first order kinetics.

After a certain lag time, backbone structures are released. Unlike the release of crosslinker cleavage product, the release of the backbone structures follows sigmoidal kinetics. The released backbone is a linear chain substituted with residues formerly connected to crosslinking moieties (for instance side chains terminating with carboxylic acids) and the functional group moiety. FIG. 3 shows schematically a partially degraded (FIG. 3a) and a fully degraded (FIG. 3b) MHP.

It is desirable to prolong the lag time to such an extent, that almost all drug release (>90%) has occurred before a significant amount of release of the backbone (<10%) has taken place. This lag time can be controlled by adjusting the number of crosslinks and the halflife of the biodegradable bond. The lag time can be increased by incorporating more crosslinks per backbone and increasing the half-life of the biodegradable bond. The effect of an increased lag time by increasing the number of crosslinks is shown in FIG. 10.

EXAMPLES

Figure 1:
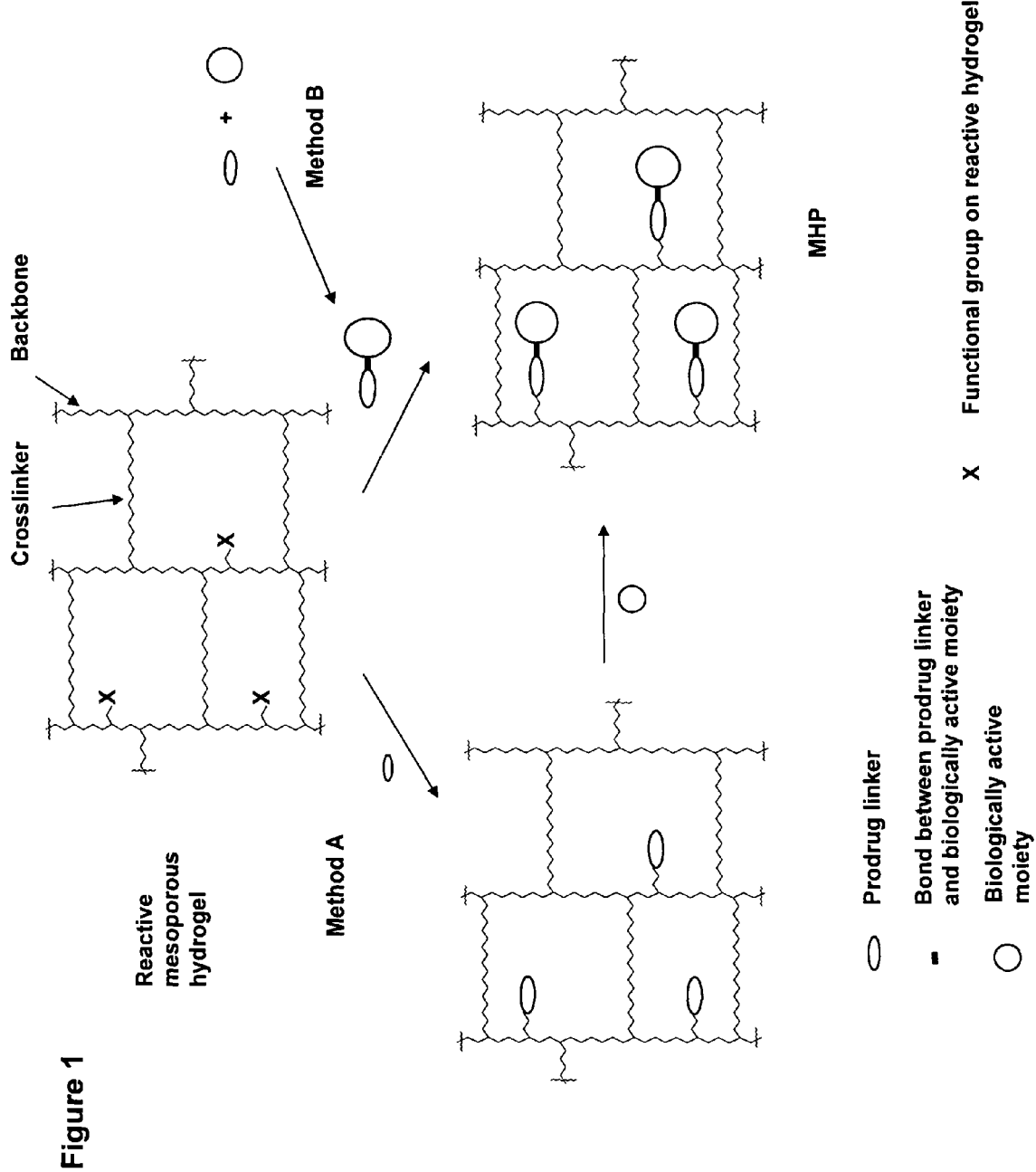
FIG. 1 shows the preparation process for mesoporous hydrogel prodrugs
Figure 2:
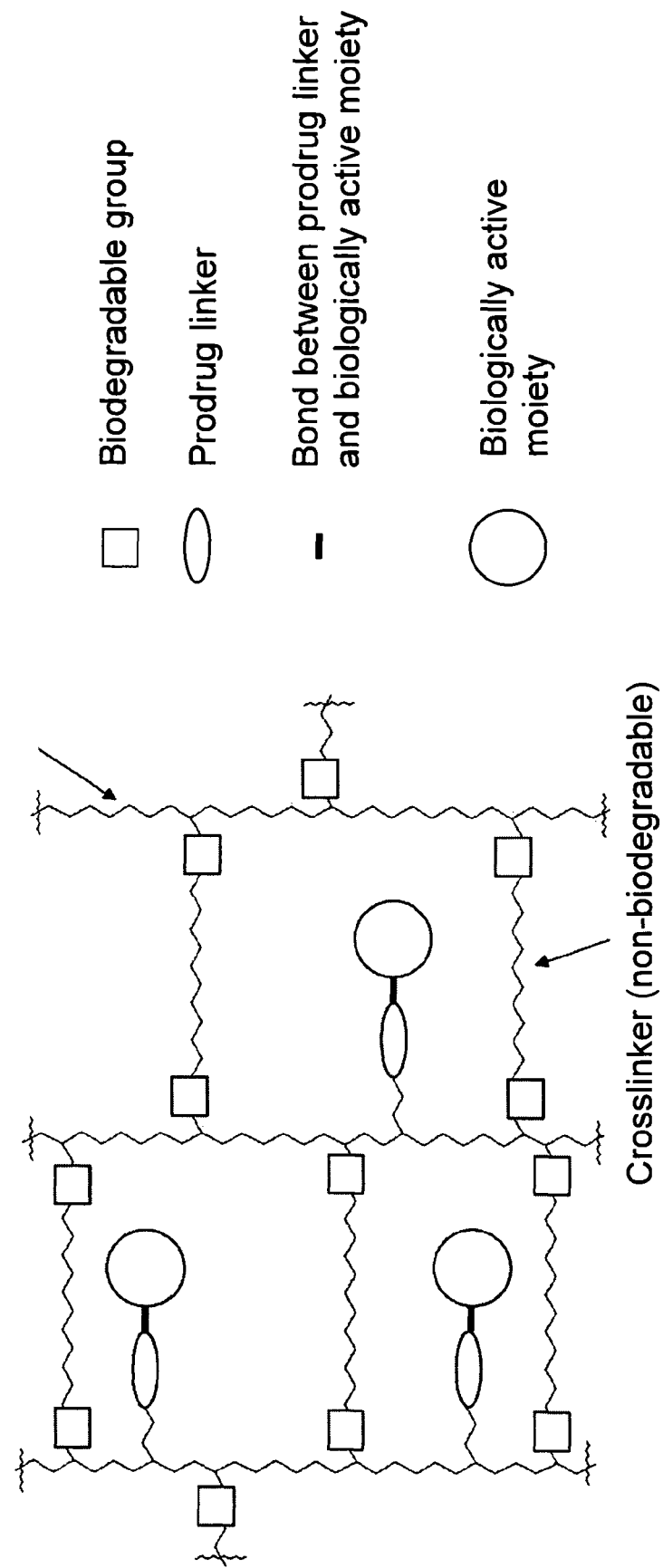
FIG. 2 shows schematically the structure of biodegradable mesoporous hydrogel prodrugs
Figure 3:
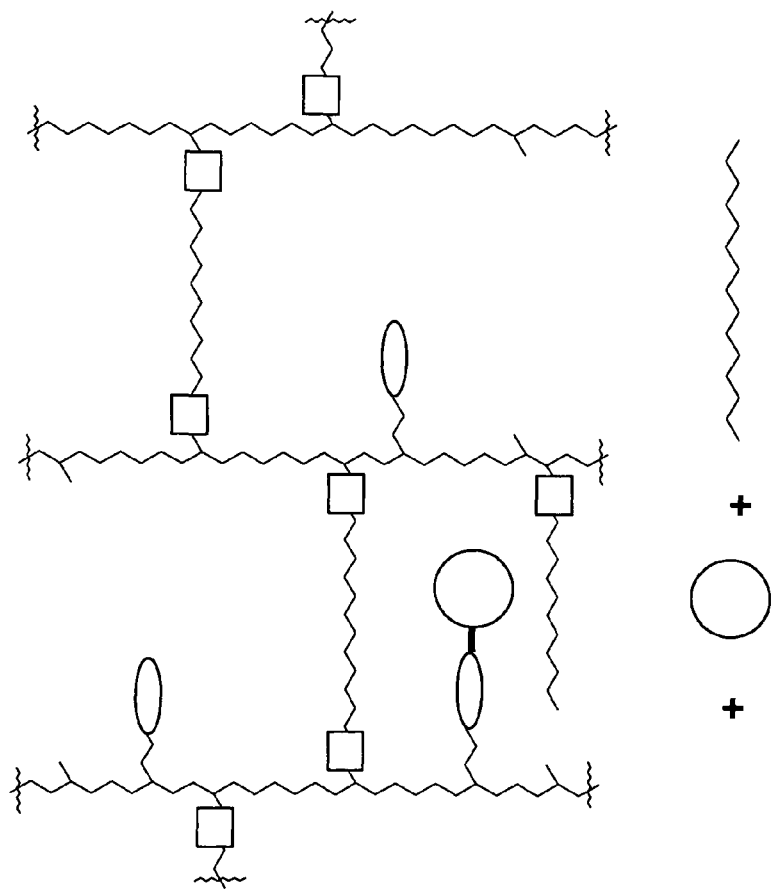
FIG. 3 shows the degradation process of biodegradable mesoporous hydrogel prodrugs
Figure 4:
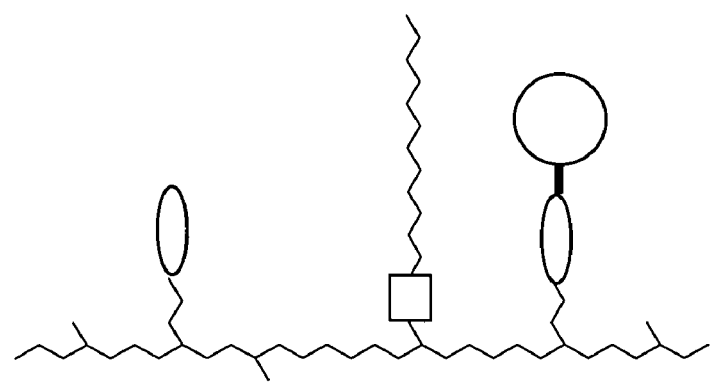
FIG. 4 shows schematically an undesired polymer modified prodrug

Maleimide Derivatization of Polyacrylamide Based Non-Biodegradable Reactive Mesoporous Hydrogel (Amino-PEGA)

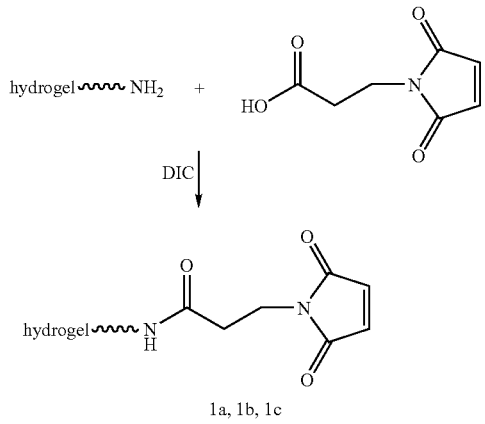

1a, 1b, 1c

Non-biodegradable mesoporous NH$_2$-PEGA hydrogel beads with 0.4 mmol/g loading and 150-300 μm bead size were purchased from Novabiochem. NH$_2$-PEGA Versamatrix-800 hydrogel beads with 0.31 mmol/g loading and 80-100 μm bead size were obtained from Versamatrix (Denmark).

2.5 g methanol-wet NH$_2$-PEGA-hydrogel (0.4 mmol/g NH$_2$-loading) was weighed into a syringe equipped with a polypropylene frit. Maleimide loading was adjusted by acylation employing a mixture of activated maleimidopropionic acid and acetic acid as described in the following. The hydrogel was washed 5 times with DMF and reacted with 13.5 mg (0.08 mmol) 3-maleimidopropionic acid, 115.2 μl (1.92 mmol) acetic acid and 313 μl (2 mmol) DIC in 4 ml DMF for 30 min. The maleimide derivatized hydrogel 1a was washed 10 times with DMF and DCM and finally with acetonitrile.

Hydrogel 1b was synthesized following the protocol above with the following modification. 2.5 g methanol-wet NH$_2$-PEGA-hydrogel (~250 mg dry resin) was reacted with 6.8 mg (0.04 mmol) 3-maleimidopropionic acid, 117.6 μl (1.96 mmol) acetic acid and 313 μl (2 mmol) DIC in 4 ml DMF for 30 min. Finally the hydrogel was washed as described. Hydrogel 1c was synthesized following the protocol above with the following modification. 2 g methanol-wet NH$_2$-PEGA Versamatrix-800 hydrogel (0.31 mmol/g NH$_2$-loading, dry resin) was washed as described and reacted with 25.3 mg (0.15 mmol) 3-maleimidopropionic acid, 115.2 μl (1.85 mmol) acetic acid and 313 μl (2 mmol) DIC in 4 ml DMF for 30 min. Finally the hydrogel was washed as described.

Synthesis of rh-insulin Loaded PEGA Hydrogel 4 and 5a,b

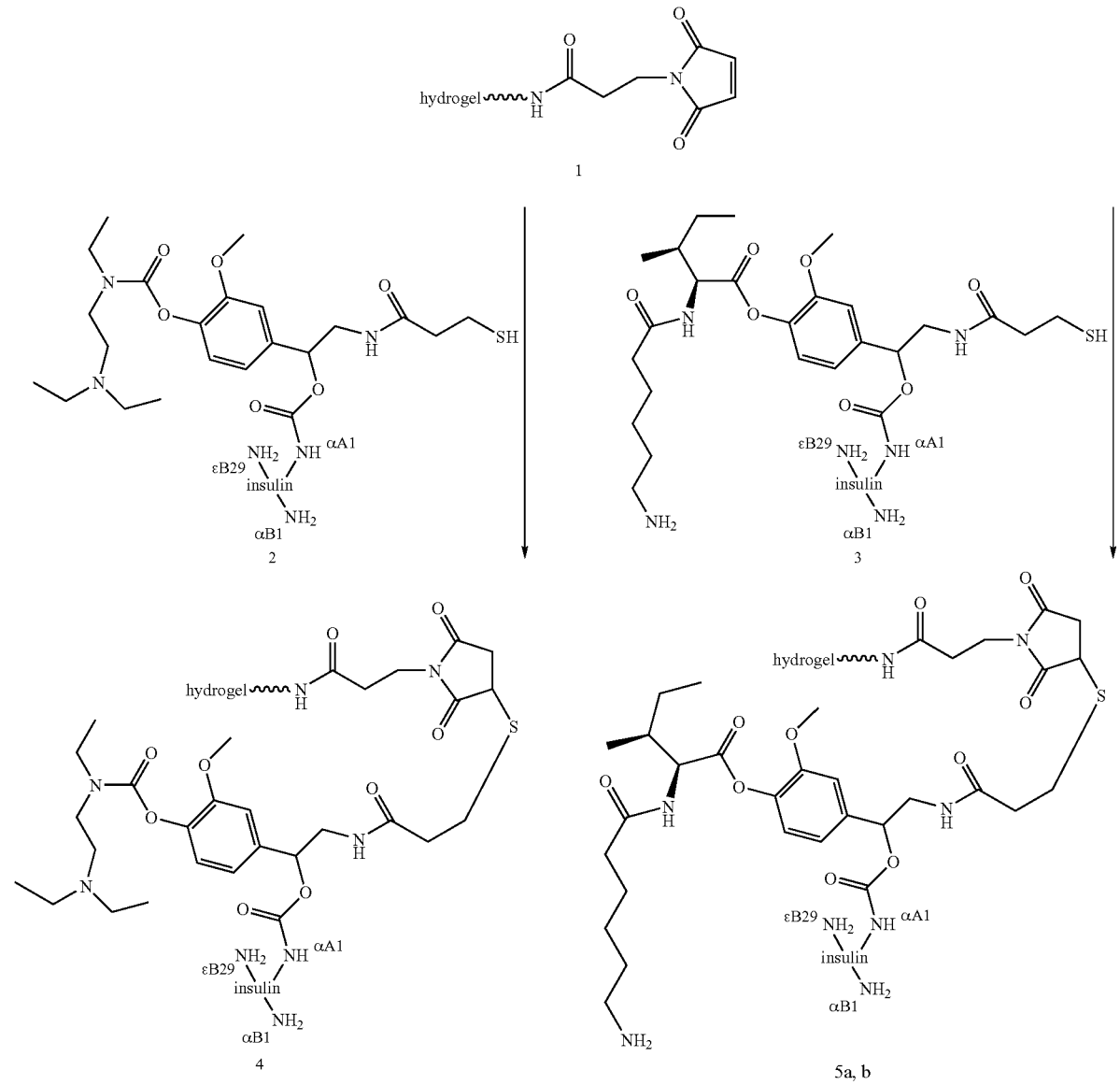

2 and 3 were synthesized as described in co-pending UK patent application No. 0415043.9 30 mg of maleimide derivatized resin 1b (loading 15 μmol/g, 450 nmol) was reacted with 3 mg of compound 2 (480 nmol, 1.06 eq) in 600 μl 20/80 (v/v) acetonitrile/50 mM phosphate buffer (pH 7.4) for 10 min to give rh-insulin loaded hydrogel 4. The hydrogel 4 was washed 5 times with 50/50 (v/v) acetonitrile/water and three times with acetonitrile and dried under vacuum.

Synthesis of hydrogel 5a or 5b by reacting 1 equivalent compound 3 in relation to the theoretical amount of maleinude groups on the hydrogel with hydrogel 1b or 1c, respectively, followed the synthesis protocol above.

In vitro rh-insulin Release Experiments from Non-Biodegradable Mesoporous Hydrogel Prodrug 4

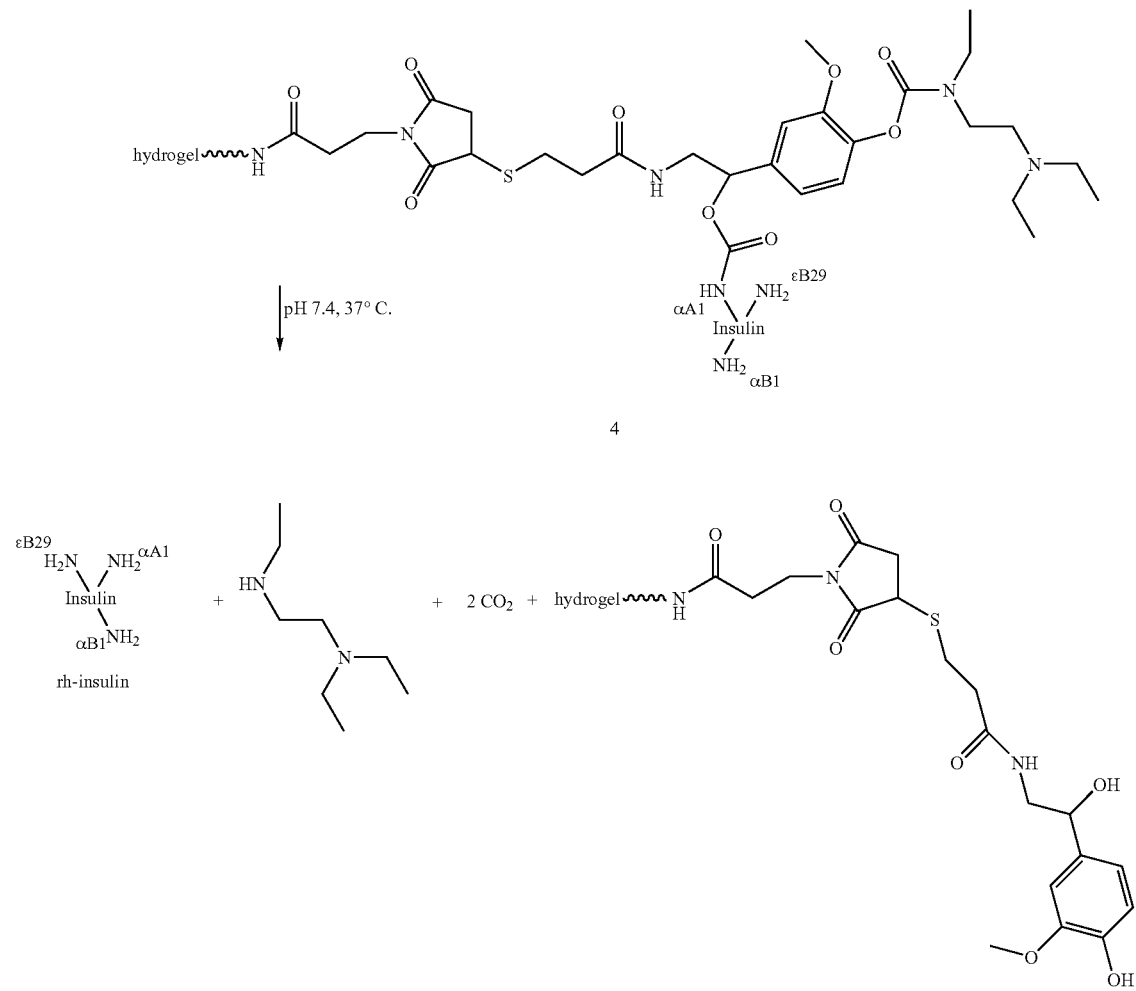

Figure 5:
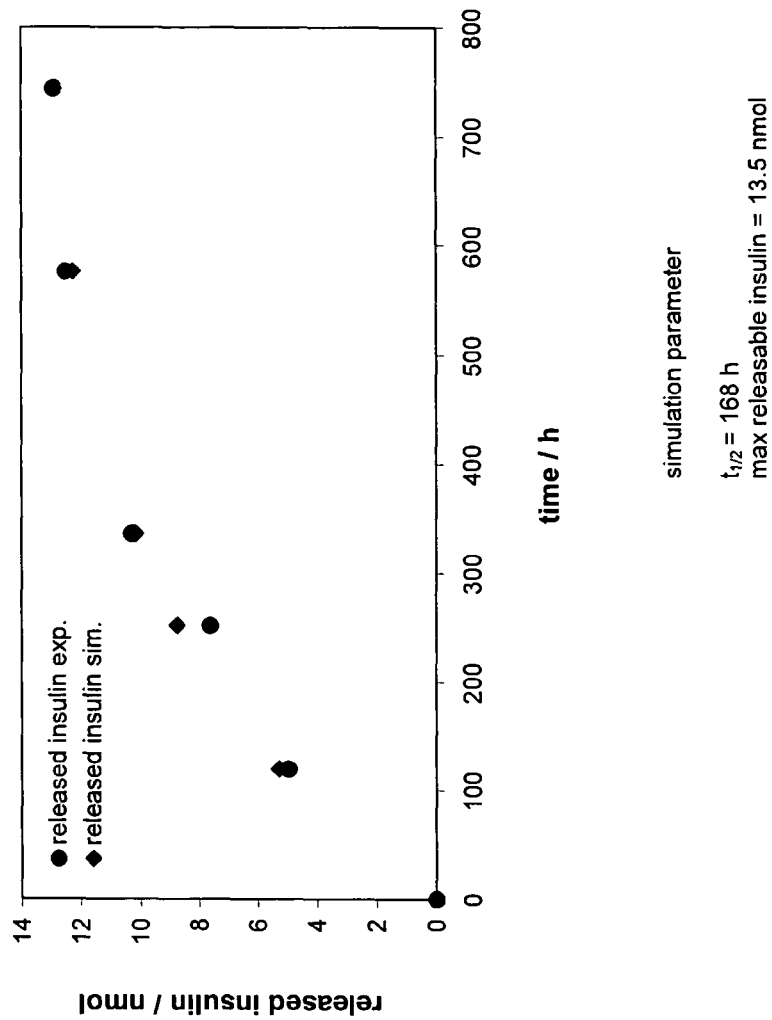
FIG. 5 shows the insulin release from a polyacrylamide-based mesoporous hydrogel prodrug

4 mg of 4 was weighed into a test tube and incubated with 1000 µl 10 mM HEPES buffer pH 7.4, 150 mM NaCl, 0.005% Tween at 37° C. 45 µl samples were taken at regular intervals and quantitatively analyzed for rh-insulin by a RP-HPLC assay. The rh-insulin peak was integrated and rh-insulin concentration was obtained from a standard curve. A first order release kinetic was fitted to the data points to give the linker half life and maximal rh-insulin release at t=∞ (FIG. 5).

Release of rh-insulin from PEGA hydrogel 5a or 5b was carried out as described above.

In vivo Release Experiments of rh-insulin from Non-Biodegradable Mesoporous Hydrogel Prodrugs 4 and 5a In vivo studies were conducted at the "Steinbeis-Transfer-Zentrum Biopharmazie und Analytik-Heidelberg" in male and female Wistar rats.

Figure 7:
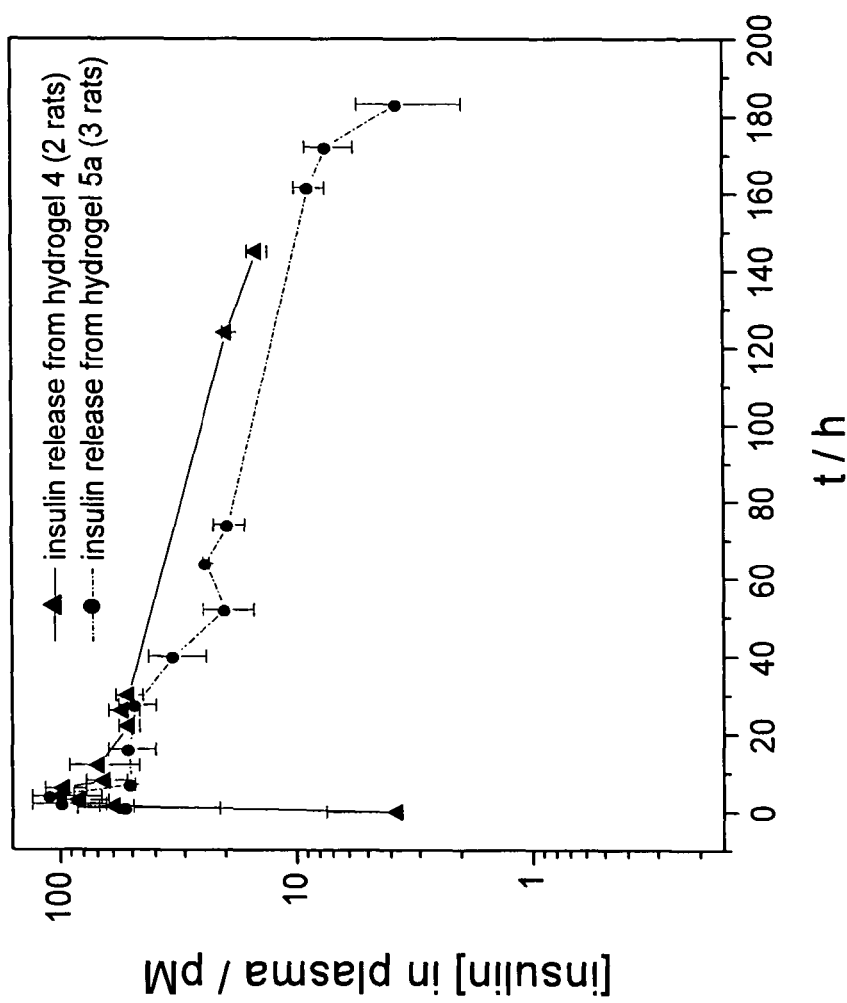
FIG. 7 shows the in vivo release of insulin from mesoporous hydrogel prodrugs

The rats weighing 200-300 g were kept under standard conditions and fed ad libitum. Blood samples (150 µl) were collected from the retro-orbital plexus and a suspension of rh-insulin loaded hydrogel in 300-400 µl PBS was subcutaneously administered in the upper hind leg area. Blood was drawn at different times after administration. Animals were lightly anesthetized by inhaled isoflurane during all blood draws and injections. All blood samples were collected into tubes containing EDTA and centrifuged. Plasma was separated and stored at −18° C. until assayed. rh-Insulin concentration was determined from plasma samples using the species specific sandwich human insulin ELISA kit (Nercodia, Sweden). The results were statistically analyzed and plasma rh-insulin concentrations were plotted over time after administration (FIG. 7).

| Hydrogel | Sample volume | Hydrogel dose/rat | Total rh-insulin dose/rat (calculated from in vitro release) | N rats |
|---|---|---|---|---|
| 5a | 400 µl | 9 mg | ~26 nmol | 3 |
| 4 | 300 µl | 10.7 mg | ~38 nmol | 2 |

Explantation of Administered Mesoporous Hydrogel Prodrug 5b and Investigation of rh-insulin Integrity Hydrogel administration, blood sampling and determination of the rh-insulin concentration followed the protocol described above.

| Hydrogel sample | Sample volume | Hydrogel dose | Total rh-insulin dose/rat (calculated from in vitro release) | N rats |
|---|---|---|---|---|
| 5b | 400 µl | 16 mg | ~138 nmol | 1 |

Figure 9:
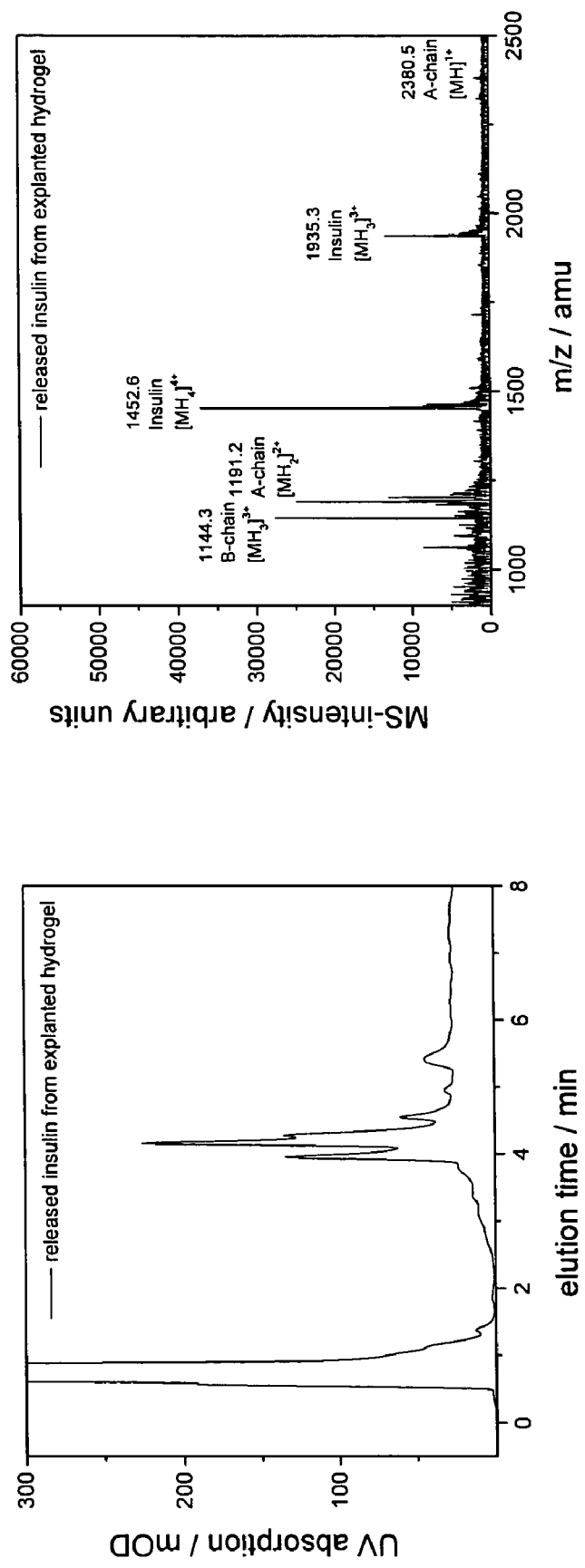
FIG. 9 shows the LCMS characterization of released insulin after explantation

After 6 days the rat was sacrificed. The hydrogel was explanted and washed 10 times with water, 10 times with 50/50 (v/v) acetonitrile/water and dried under vacuum. About 1 mg of hydrogel was weighed into a test tube and incubated with 400 µl 100 mM Tris/HCl buffer pH 9, at 37° C. After 24 h the solution was separated from the hydrogel and analyzed for rh-insulin and enzymatic degradation products thereof by LC/MS (FIG. 9). The strong peak at 4.2 min elution time can be assigned to rh-insulin according to the mass spectrum. Smaller peaks before and after the rh-insulin peak correspond to the A- and B-chain of rh-insulin, respectively. No rh-insulin related degradation products were detected. A- and B-chain were also detected in in vitro release experiments at pH 9 and thus do not indicate enzymatic degradation.

Synthesis of Biodegradable Reactive Mesoporous Hydrogel 8

Synthesis of Macromonomer bis-acryl-glycyl-PEG900 (6)

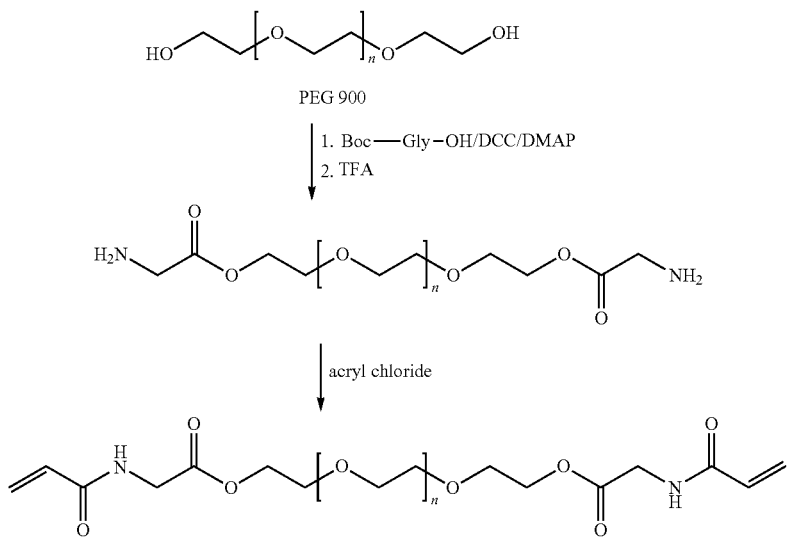

10 g PEG900 (11.1 mmol) were dissolved in 50 ml DCM and the solution was cooled to 0° C. A solution of 3.9 g (23.3 mmol) boc-glycine, 5.67 g (46.6 mmol) DMAP, and 950 mg DCC (4.6 mmol) in 50 ml DCM was added and the mixture was stirred over night at room temperature. The solid byproduct dicyclohexyl urea was filtered off and the filtrate was washed two times with 1 M HCl and two times with water. The organic phase was dried over sodium sulfate and was concentrated in vacuo to approximately 50 ml. 50 ml TFA were added at 0° C. and the solution was stirred at room temperature for 30 min to remove the boc protecting groups. The solvent was removed under reduced pressure and the resulting oil was redissolved in 50 ml DCM. 5 ml 2 M HCl in diethyl ether was added and the product precipitated by the addition of 400 ml diethyl ether and collected by centrifugation. The resulting oil was dissolved in 100 ml 0.1 M aqueous HCl and lyophilized (yield: 9.5 g) LC/MS: [M+H]$^+$=882.3, 926.4, 970.4, 1014.4, 1058.4, 1102.5, 1146.6 (MW+H calculated=1014.2±x*44.05 g/mol)

1.4 g bis-glycyl-PEG900 were dissolved in 15 ml DCM and 750 µl (5.32 mmol) triethylamin and 220 µl (2.66 mmol) acryl chloride were added at 0° C. The mixture was stirred at room temperature for 30 min and 35 ml DCM were added. The organic phase was washed with 1 M aqueous HCl and 5 times with water. The organic phase was dried over sodium sulfate and concentrated under reduced pressure to approximately 10 ml. The product 6 was precipitated by the addition of 60 ml 1/1 (v/v) diethyl ether/heptane and collected by centrifucation (yield 1.05 g).

LC/MS: [M+Na]$^+$=1012.0, 1056.6, 1100.5, 1144.5, 1188.6, 1232.5, 1275.6, 1319.7 (MW+Na calculated=1144.2±x*44.05 g/mol)

Synthesis of N-boc,N'-acryloyl-4,7,10-trioxatridecane-1,13-diamine

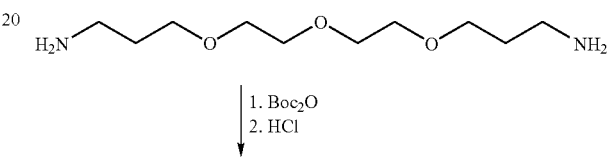

-continued

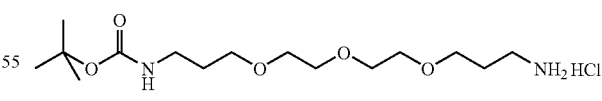

2 g (9.1 mmol) 4,7,10-trioxatridecane-1,13-diamine were dissolved in 15 ml DCM and 1 g (4.6 mmol) di-tert.-butyl-dicarbonate in 10 ml DCM was added dropwise at 0° C. The solution was stirred for 2 h at room temperature and the organic phase was washed five times with water. The organic diethyl ether/heptane and collected by centrifugation. (yield: 940 mg, 2.5 mmol, 78%).

LC/MS: [M+Na]$^+$=398.1 (MW+Na calculated=397.4 g/mol)

Biodegradable Reactive Mesoporous Hydrogel Formation

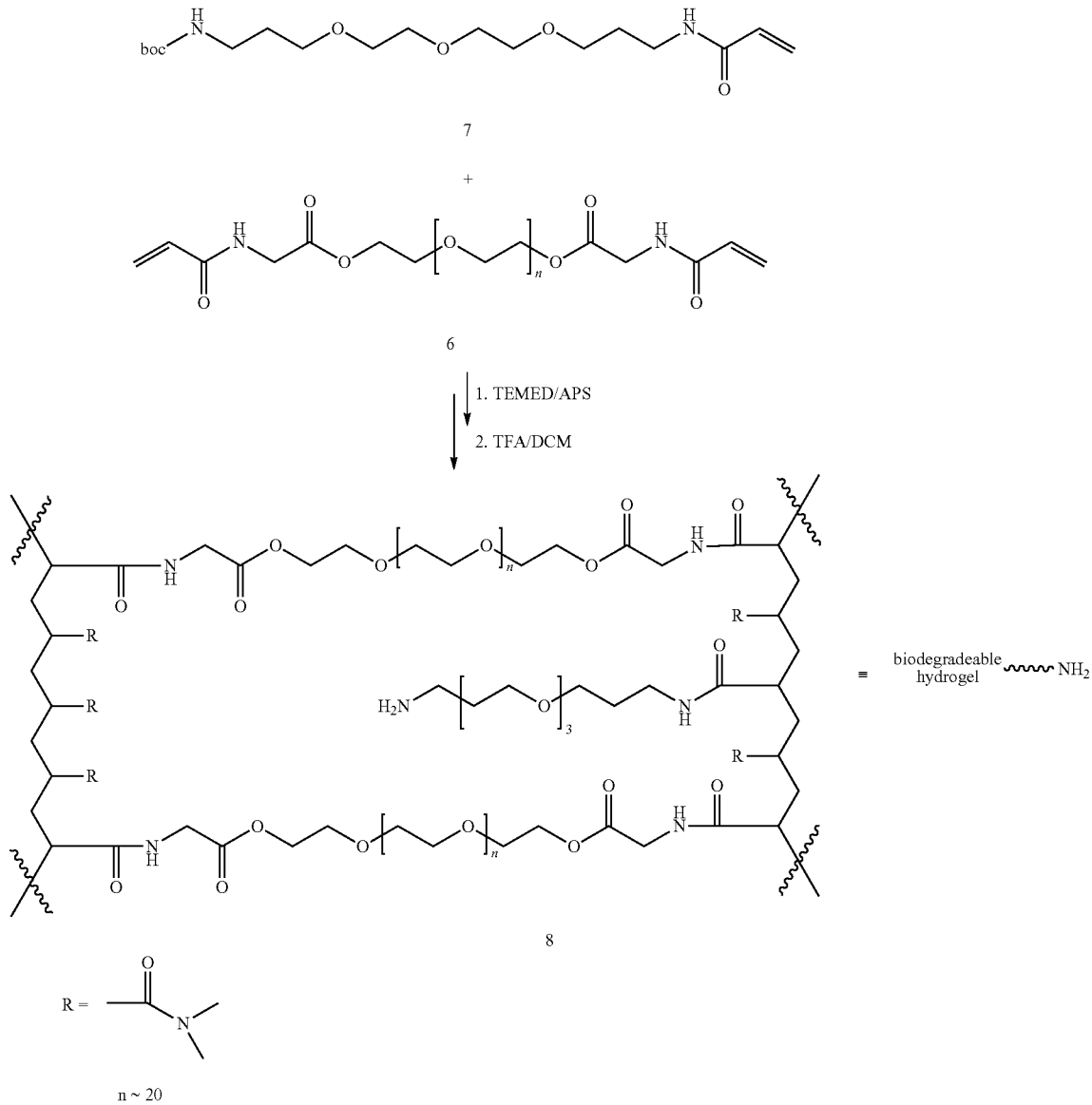

phase was dried over sodium sulfate and concentrated under reduced pressure to approximately 10 ml. Mono-boc-4,7,10-trioxatridecane-1,13-diamine was precipitated as hydrochloride salt by the addition of 2 M HCl in diethyl ether (yield: 1.1 g, 3.1 mmol, 67%).

1.1 g (3.1 mmol) mono-boc-4,7,10-trioxatridecane-1,13-diamine was dissolved in 10 ml DCM and 900 µl (6.2 mmol) triethylamine was added. The mixture was cooled to 0° C. and 260 µl (3.2 mmol) acryl chloride in 10 ml DCM was added dropwise. The solution was stirred at room temperature for 30 min and the organic phase was washed two times with 0.1 M aqueous HCl. The organic phase was dried over sodium sulfate and concentrated to 7 ml under reduced pressure. The product 7 was precipitated by the addition of 50 ml 1/1 (v/v)

100 mg (100 µmol) compound 6, 6 mg (15 µmol) compound 7 and 21 mg (212 µmol) N,N-dimethylacrylamide were dissolved in 500 µl 50 mM phosphate buffer (pH 7.0) in a test tube. After addition of 30 µl 1 M ammonium peroxodisulfate (APS), the solution was vortexed and polymerization was initiated by addition of 80 µl 2 M N,N,N',N'-tetramethylethylenediamine (TEMED)/HCl, pH 7.0. The spontaneously formed hydrogel was incubated for further 30 min, ground to particles <1 mm and transferred into a syringe equipped with a polypropylene frit. After extensive washing of the hydrogel with water, DMF and DCM (5 times each), boc-protecting groups were cleaved by incubation with (v/v) 50/50 TFA/DCM for 10 min. Finally, the hydrogel 8 was washed five times with DCM, five times with DMF, once with 1/99 (v/v) DIEA/DMF and five times with DMF.

Synthesis of Maleimide Derivatized Biodegradable Polyacrylamide Based Mesoporous Hydrogel 9

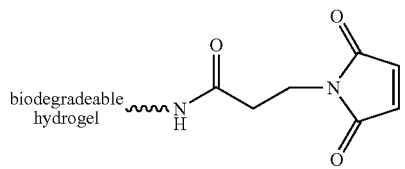

100 mg ground biodegradable hydrogel 8 was weighed into a syringe equipped with a polypropylene frit. Maleimide derivatization was achieved by acylation with 101 mg (0.6 mmol) maleimidopropionic acid, 94 µl (0.6 mmol) DIC in 2 ml DMF for 30 min to give maleimide derivatized hydrogel 9. The hydrogel was washed 10 times with DMF and DCM.

Synthesis of fluorescein-carboxamido-Lys(B29)-rh-insulin Loaded Biodegradable Polyacrylamide Based Mesoporous Hydrogel Prodrug 11

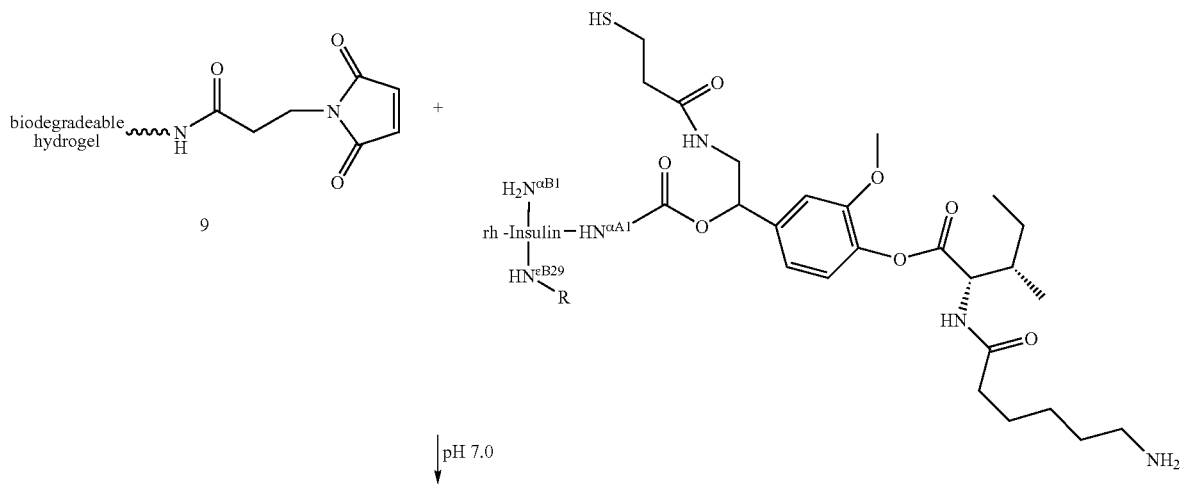

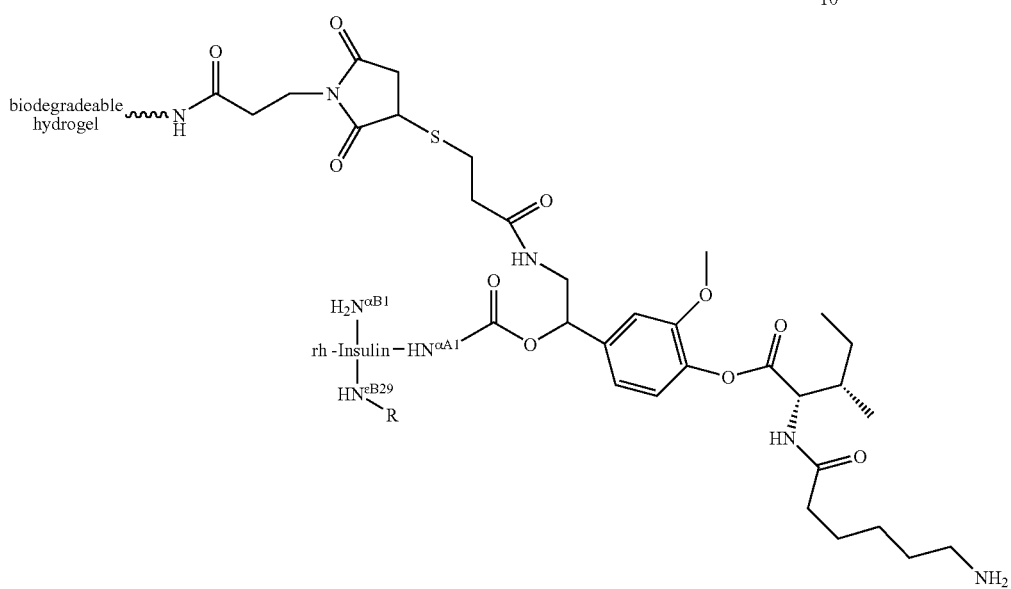

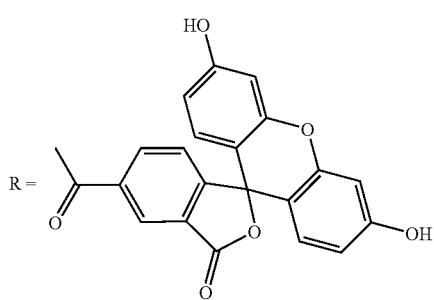

Isomer 5, 6

Compound 10 was synthesized as described in co-pending UK patent application No. 0415043.9, the disclosure of which is incorporated by reference. 0.25 mg of compound 10 (35 nmol) was dissolved in 100 μl 40/40/20 (v/v/v) acetonitrile/water/0.5 M phosphate buffer pH 7.0. The solution was incubated for 3 min with 5.6 mg of maleimide derivatized biodegradable hydrogel 9 to give fluorescein-carboxamido-Lys(B29)-rh-insulin loaded hydrogel 11. The hydrogel 11 was washed five times with 50/50 (v/v) acetonitrile/water, three times with acetonitrile and dried under vacuum.

In vitro fluorescein-carboxamido-Lys(B29)-rh-insulin Release Experiments from Biodegradable Polyacrylamide Based Meso Porous Hydrogel Prodrug 11

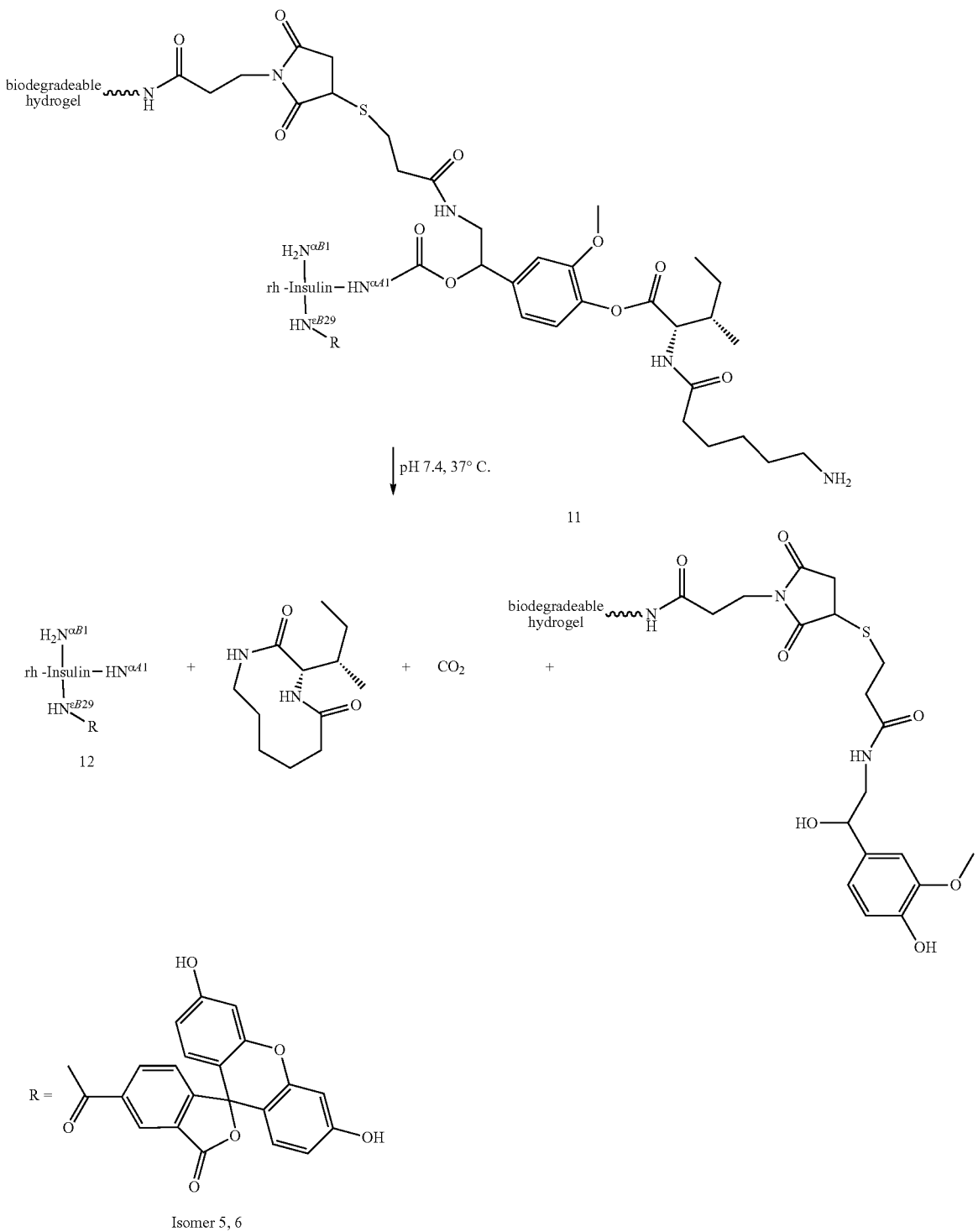

Figure 8:
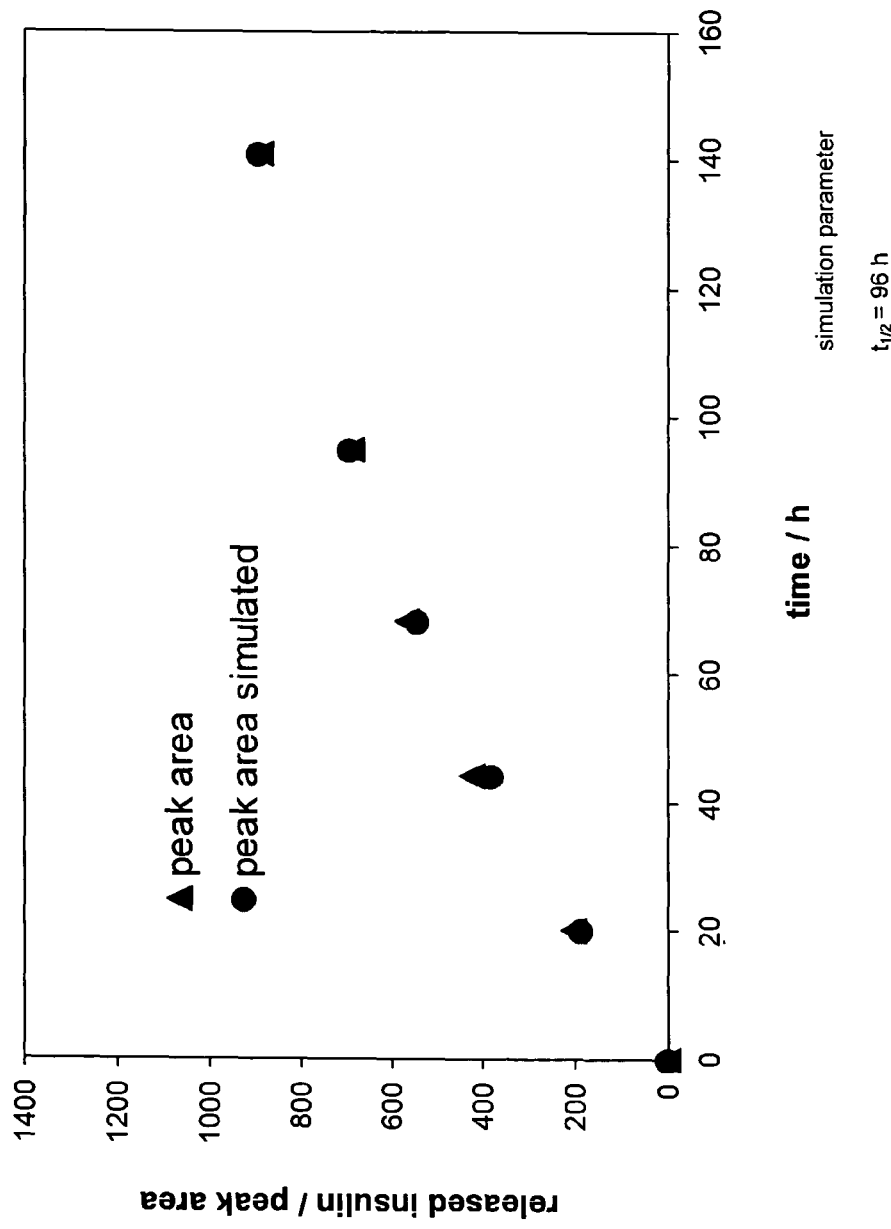
FIG. 8 shows the insulin release from a biodegradable mesoporous hydrogel prodrug

The fluorescein-carboxamido-Lys(B29)-rh-insulin loaded biodegradable hydrogel 11 was incubated in 100 μl 10 mM HEPES buffer (pH 7.4), 150 mM NaCl, 0.005% Tween at 37° C. 80 µl samples were taken at regular intervals and quantitatively analyzed for fluorescein-carboxamido-Lys(B29)-rh-insulin by a RP-HPLC assay. A first order release kinetic was fitted to the data points to give the half life of the prodrug linker and maximal fluorescein-carboxamido-Lys(B29)-rh-insulin concentration at t=∞ (FIG. 8). The integrity of the released fluorescein-carboxamido-Lys(B29)-rh-insulin 12 was confirmed by RP-LCMS and SEC (data not shown).

Synthesis of Fluorescein Labeled Compound 12

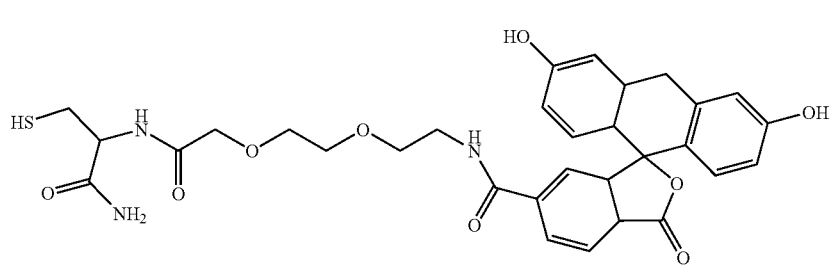

5,6-Isomers 0.3 g Sieber amide resin (loading 0.5 mmol/g) was weighed into a syringe equipped with a polypropylene frit. Fmoc-removal was achieved by incubation in 2/2/96 (v/v/v) piperidin/DBU/DMF for 10 min and the resin was washed 5 times with DMF.

The resin was incubated for 1 h with 264 mg (0.45 mmol) Fmoc-Cys(Trt)-OH, 144 mg (0.45 mmol) TBTU and 157 µl DIEA (0.9 mmol) in 3 ml DMF and washed 5 times with DMF. After fmoc-removal, Fmoc-Ado-OH was coupled by incubation of 156 mg (0.45 mmol) Fmoc-Ado-OH 173 mg (0.45 mmol) TBTU and 157 µl DIEA (0.9 mmol) in 3 ml DMF according to the procedure above. Fmoc was removed and the resin was reacted with 338 mg (0.9 mmol) 5,6-carboxyfluorescein (isomeric mixture), 140 mg (0.9 mmol) HOBt and 141 µl (0.9 mmol) DIC in 3 ml DMF for 2 h. Finally the resin was incubated in 2/2/96 (v/v/v) piperidine/DBU/DMF for 10 min, washed 10 times in DCM and dried under vacuum.

12 was cleaved from the resin with 50/5/45 (v/v/v) TFA/TES/DCM for 30 min and purified by RP-HPLC.

MS: $[MH]^+$=625 g/mol (MW calculated=624 g/mol)

Degradation of Biodegradable Polyacrylamide-Based Mesoporous Hydrogel 13 in vitro

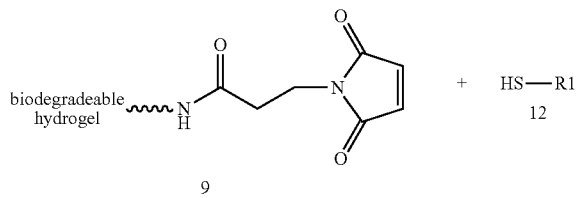

↓ pH 7.0

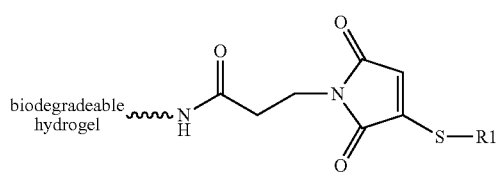

↓ pH 9.0, 37° C.

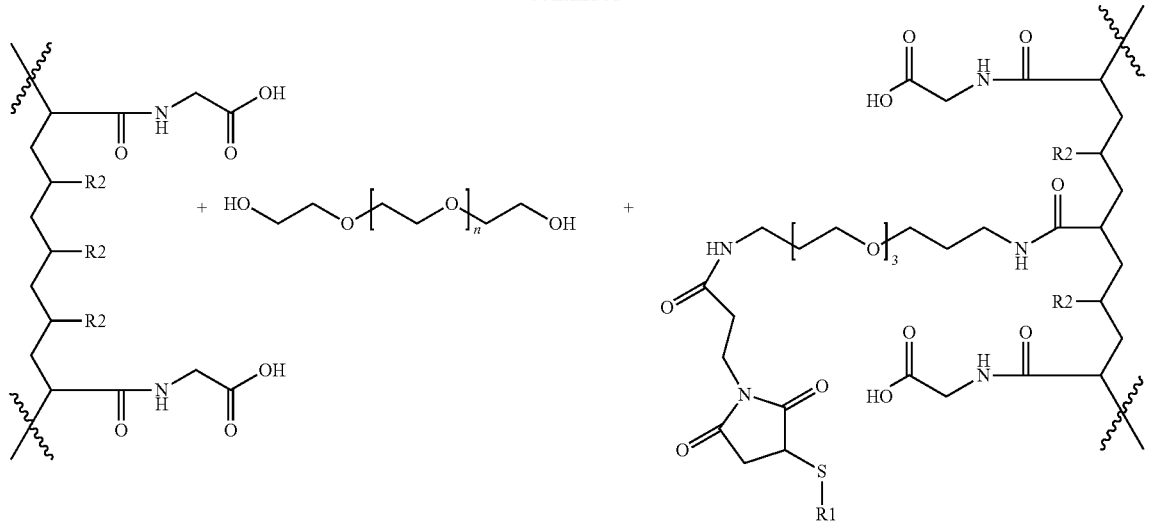

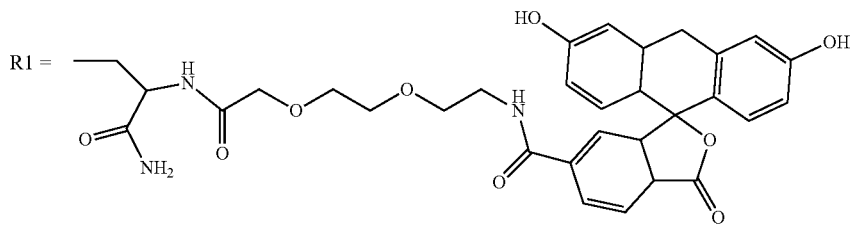

5, 6 Isomers

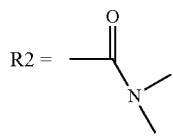

n~20

A 100 μM solution of compound 12 (35 nmol) in 500 μl 40/40/20 (v/v/v) acetonitrile/water/0.5 M phosphate buffer pH 7.0 was reacted with 5 mg of maleimide derivatized biodegradable hydrogel 9 for 5 min to give the fluorescein labeled hydrogel 13. The hydrogel 13 was washed 5 times with 50/50 (v/v) acetonitrile/water and three times with acetonitrile and dried under vaccuum.

Hydrogel degradation experiment was performed at pH 9 to reduce the time of degradation. Degradation time at physiological pH 7.4 was estimated by a scaling factor 40 that accounts for the approx. 40 fold increased hydroxide ion concentration at pH 9 compared to pH 7.4. The hydrogel was suspended in 1 ml 50 mM borate buffer (pH 9.0), 150 mM NaCl, 0.005% Tween and incubated at 37° C. 60 μl samples were taken at different time intervals and quantitatively analyzed for polymer backbone coupled fluorescein 14 by photometry at 500 nm. The data show a delayed and sigmoidal release of 14 (data not shown).

Synthesis of rh-insulin Loaded Carbohydrate-Based Mesoporous Hydrogel Prodrug 16 and in vitro Release NHS-activated "Sepharose 4 Fast Flow" hydrogel beads (chemically crosslinked agarose, crosslinker epichlorhydrin) were purchased from Amersham.

1.5 g ethanol-wet Sepharose hydrogel (150 mg dry hydrogel) was weighed into a syringe equipped with a polypropylene frit and reacted with 1 M 4,7,10-trioxatridecan-1,13-diamin in DMF for 30 min. After 5 washing steps with DMF, hydrogel was reacted with 8.5 mg (0.05 mmol) 3-maleimidopropionic acid, 57 μl (0.95 mmol) acetic acid, 151 mg (1 mmol) HOBt and 158 μl (1 mmol) DIC in 4 ml DMF for 30 min to give maleimide derivatized hydrogel 15. The hydrogel 15 was washed 10 times with DMF and finally with acetonitrile. 1.5 mg 3 was dissolved in 25/75 (v/v) acetonitrile/50 mM phosphate buffer pH 7.4 and reacted with 10.8 mg maleimide derivatized hydrogel 15 for 10 min. The rh-insulin loaded hydrogel 16 was washed five times with 50/50 (v/v) acetonitrile/water and three times with acetonitrile and dried under vacuum.

Figure 6:
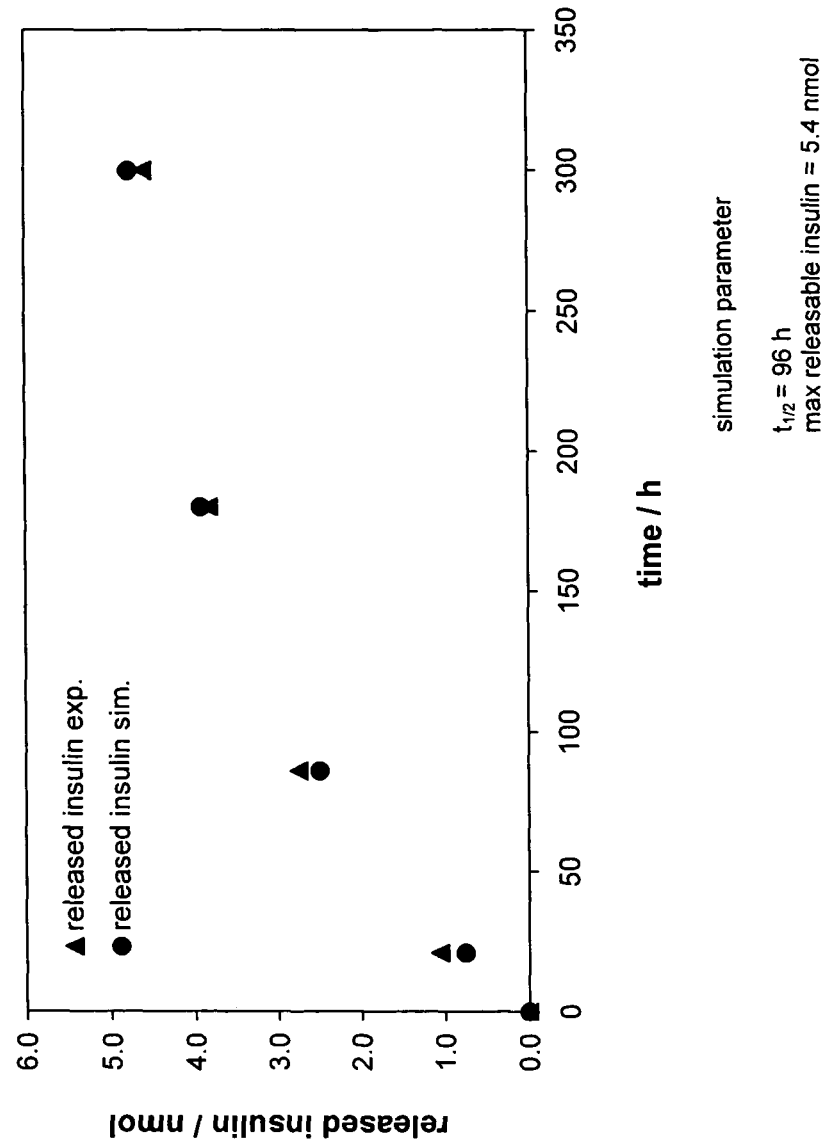
FIG. 6 shows the insulin release from a carbohydrate-based mesoporous hydrogel prodrug

2 mg rh-insulin-loaded hydrogel 16 was suspended in 1000 μl 10 mM HEPES buffer (pH 7.4), 150 mM NaCl, 0.005% Tween and incubated at 37° C. 60 μl samples were taken at regular intervals and quantitatively analyzed for rh-insulin by an RP-HPLC assay. A first order release kinetic was fitted to the data points to give the half life of the prodrug linker and maximal rh-insulin release at $t=\infty$ (FIG. 6). The integrity of the released rh-insulin was confirmed by LCMS (data not shown).

Synthesis of Biodegradable Mesoporous Hydrogel 20 and 21
Synthesis of bis-mercaptoacetyl-glycyl-PEG900 (17)

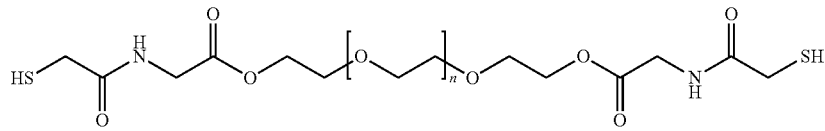

17

1 g (0.92 mmol) bis-glycyl-PEG900×2HCl was dissolved in 7 ml DMF and 600 mg (2 mmol) SAMA-OPfp ester was added. The mixture was stirred at room temperature for 60 min. 200 μl hydrazin hydrate was added and the mixture stirred for 5 min at room temperature to remove the acetyl group. After addition of 400 μl acetic acid the product 17 was purified by RP-HPLC and lyophilized (yield 740 mg).

LC/MS:
$[M+H]^+$=1030.2, 1074.2; 1118.3; 1162.2; 1206.3; 1250.3; 1294.4, 1338.4 (MW+H calculated=1161.4±x*44.05 g/mol)

Synthesis of 1-naphtylacetyl-tetra-Lys(Ado-mp)-amide (18) and 1-naphtylacetyl-octa-Lys(Ado-mp)-amide (19)

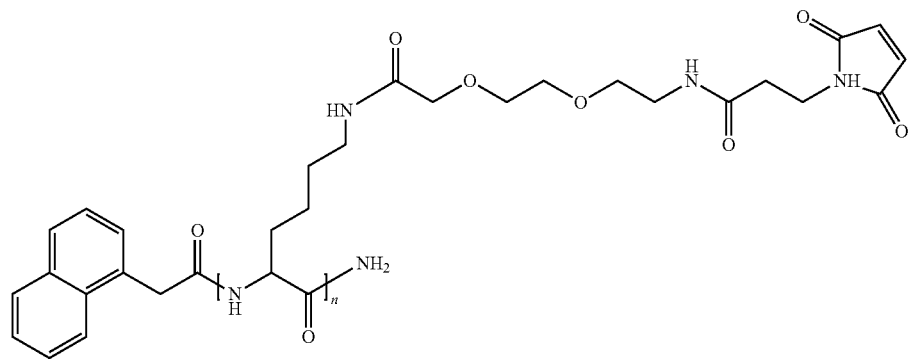

18: n = 4
19: n = 8

18 was synthesized by standard solid-phase organic synthesis using TBTU/DIEA activation as described for compound 12.

To 1 g TentaGel Sieber amide resin (0.17 mmol/g loading) four times Fmoc-Lys(ivDde)-OH and 1-naphthyl acetic acid was coupled by TBTU/DIEA activation using 3 equivalents amino acid in relation to free amino groups on the resin. To remove the ivDde protecting group the resin was incubated three times with 4% hydrazine in DMF for 7 min. After washing of the resin with DMF, Fmoc-Ado-OH was coupled to the amino groups by TBTU/DIEA activation. 3-maleimidopropionic acid was coupled by DIC activation using 3 equivalents 3-maleimidopropionic acid in relation to free amino groups on the resin. Compound 18 was cleaved from the resin by incubation with 94/3/3 (v/v/v) DCM/triethylsilane/TFA for 60 min. After evaporation of the solvent, 18 was purified by RP-HPLC and lyophilized.

19 was synthesized as described above by coupling eight Fmoc-Lys(ivDde)-OH residues instead of four residues.

LC/MS:
n=4:
$[M+H]^+$=1883.9; $[M+Na]^+$=1905.2 (MW calculated=1879.1 g/mol)
n=8:
$[M+2Na]^{2+}$=1812; $[M+H+Na]^{2+}$=1800; $[M+2H]^{2+}$=1790 (MW calculated=3573.0 g/mol)

Biodegradable Hydrogel 20 and 21 Formation
17 + 18 →(pH 5.5)
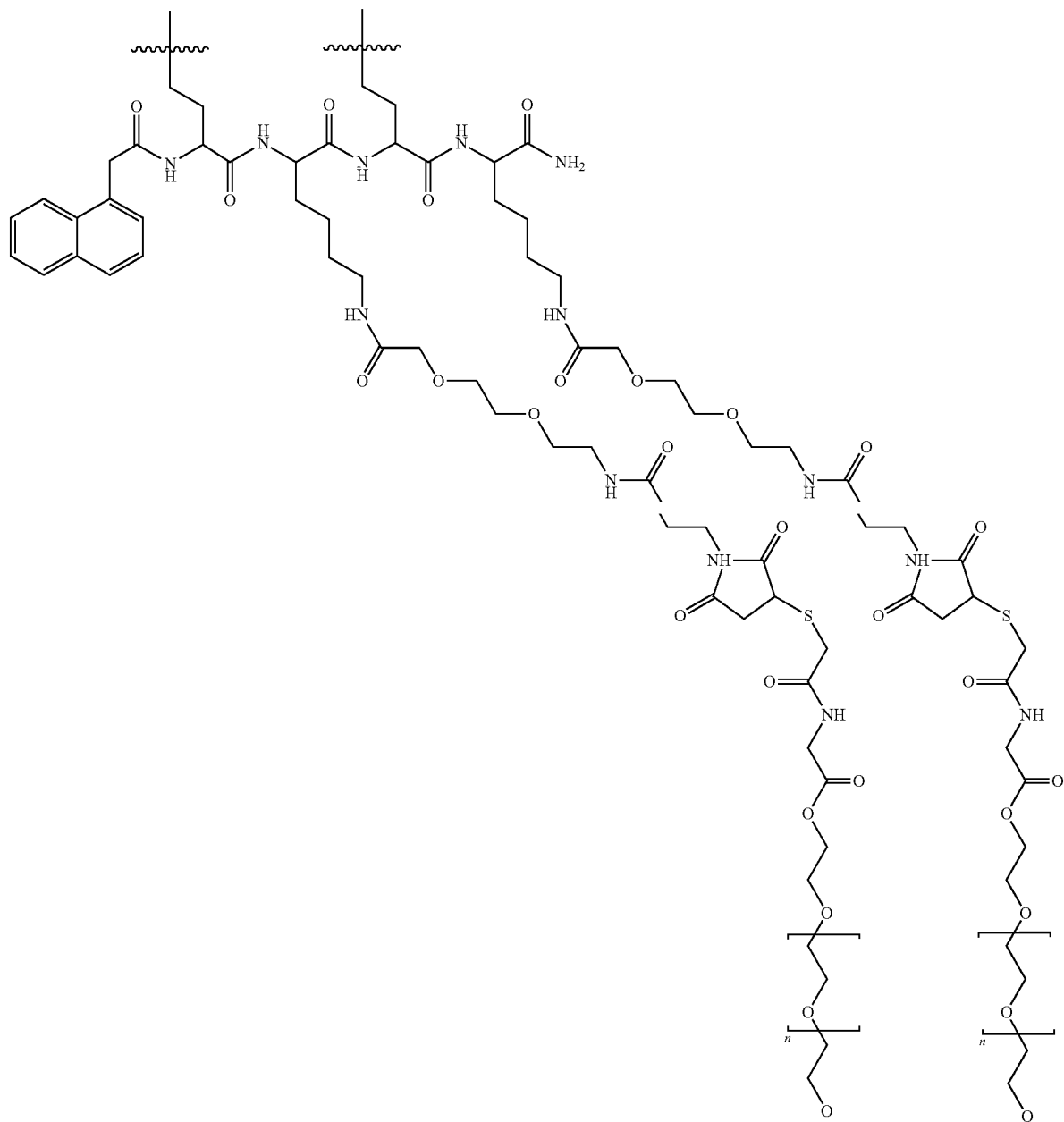

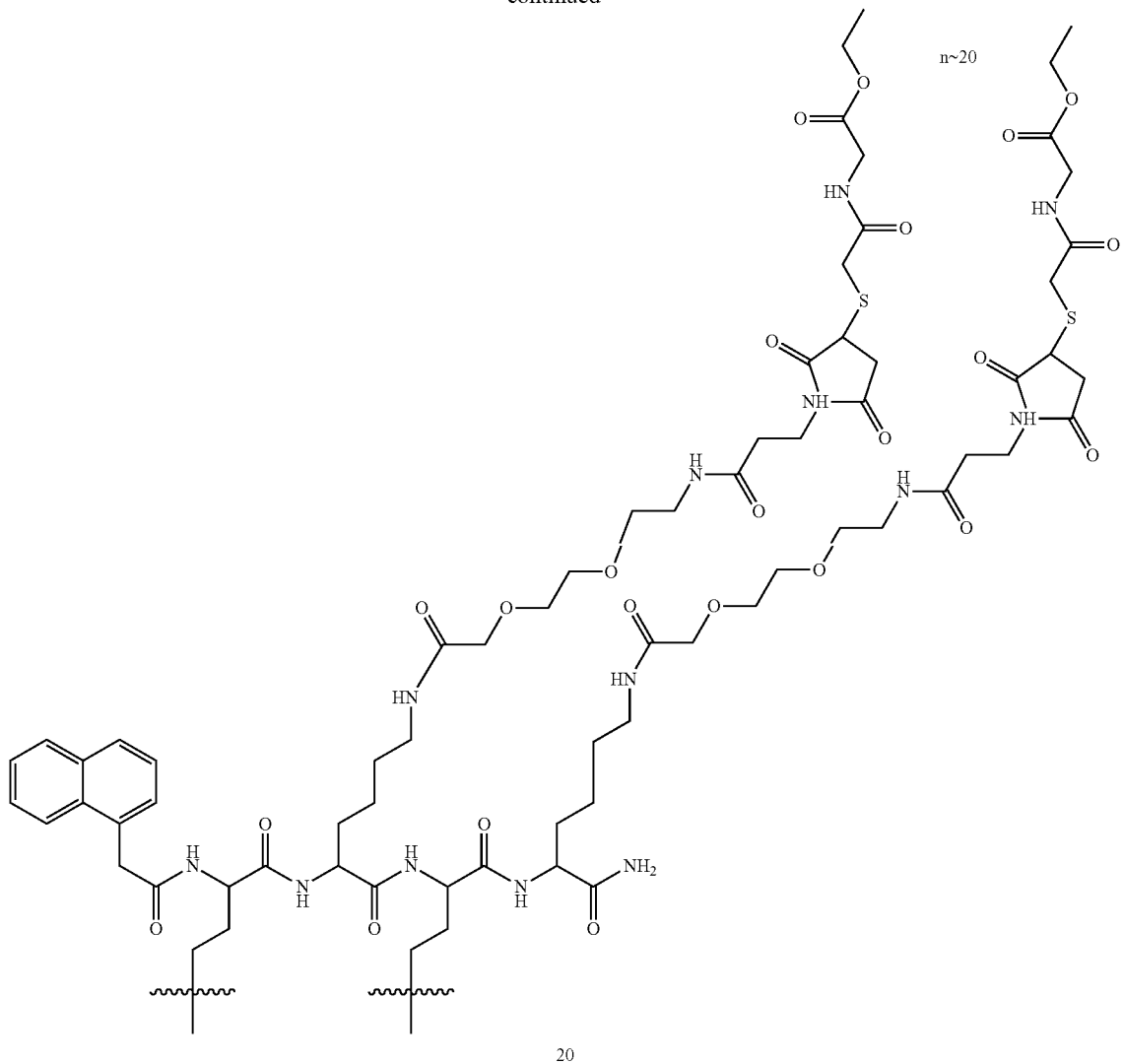

20

23.2 mg (20 μmol) 17 and 18.8 mg (10 μmol) 18 were dissolved in 150 μl water and 50 μl 0.5 M sodium acetate buffer pH 5.5 were added. The solution was incubated at room temperature for 60 min.

The resulting hydrogel 20 was ground to particles <1 mm and transferred into a syringe equipped with a polypropylene frit. The hydrogel particles were washed five times each with 1/1 acetonitrile/water, water, and methanol and then dried under vacuum. Hydrogel 21 was synthesized as described above using 23.3 mg (20 μmol) 17 and 17.9 mg (5 μmol) 19.

Degradation Study 20 or 21

↓ pH 9, 37° C.

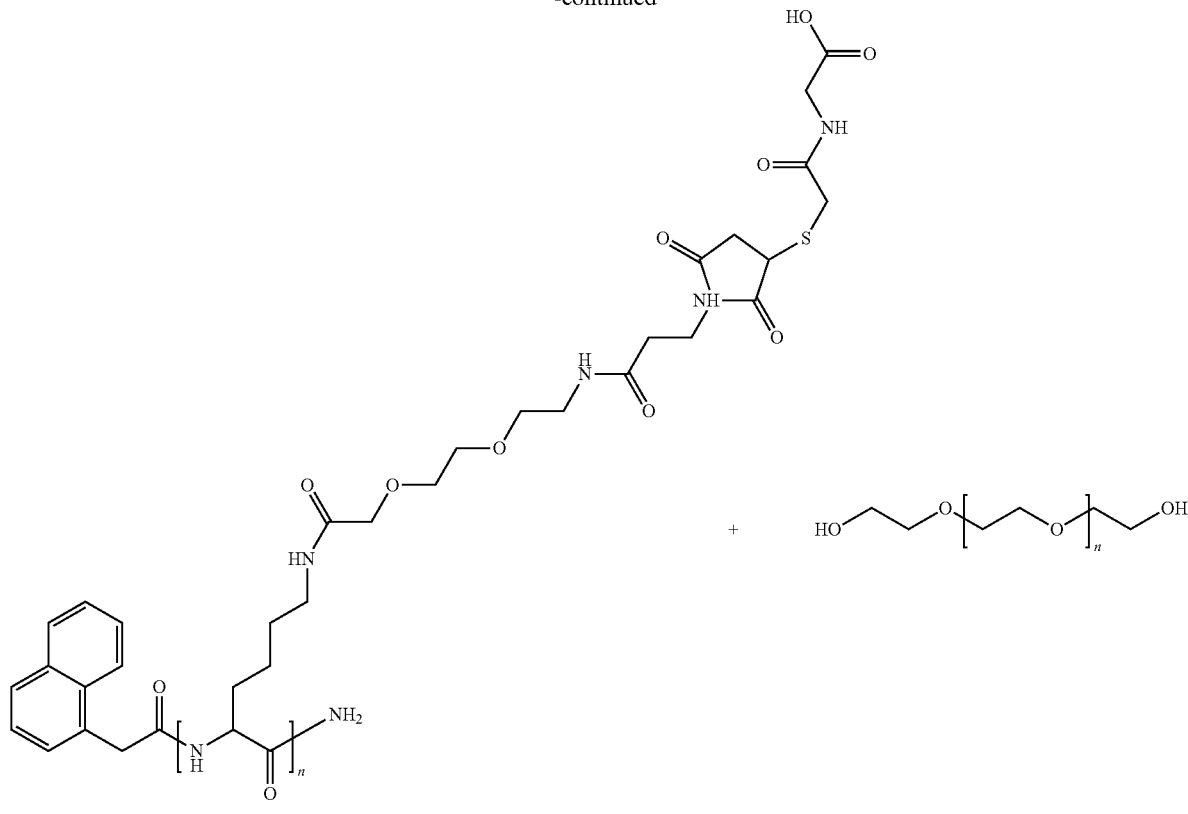

22: n = 4
23: n = 8

Hydrogel degradation experiments were performed at pH 9 to reduce the time of degradation. Degradation time at physiological pH 7.4 was estimated by a scaling factor 40 that accounts for the ~40 fold increased hydroxide ion concentration at pH 9 compared to pH 7.4.

Figure 10:
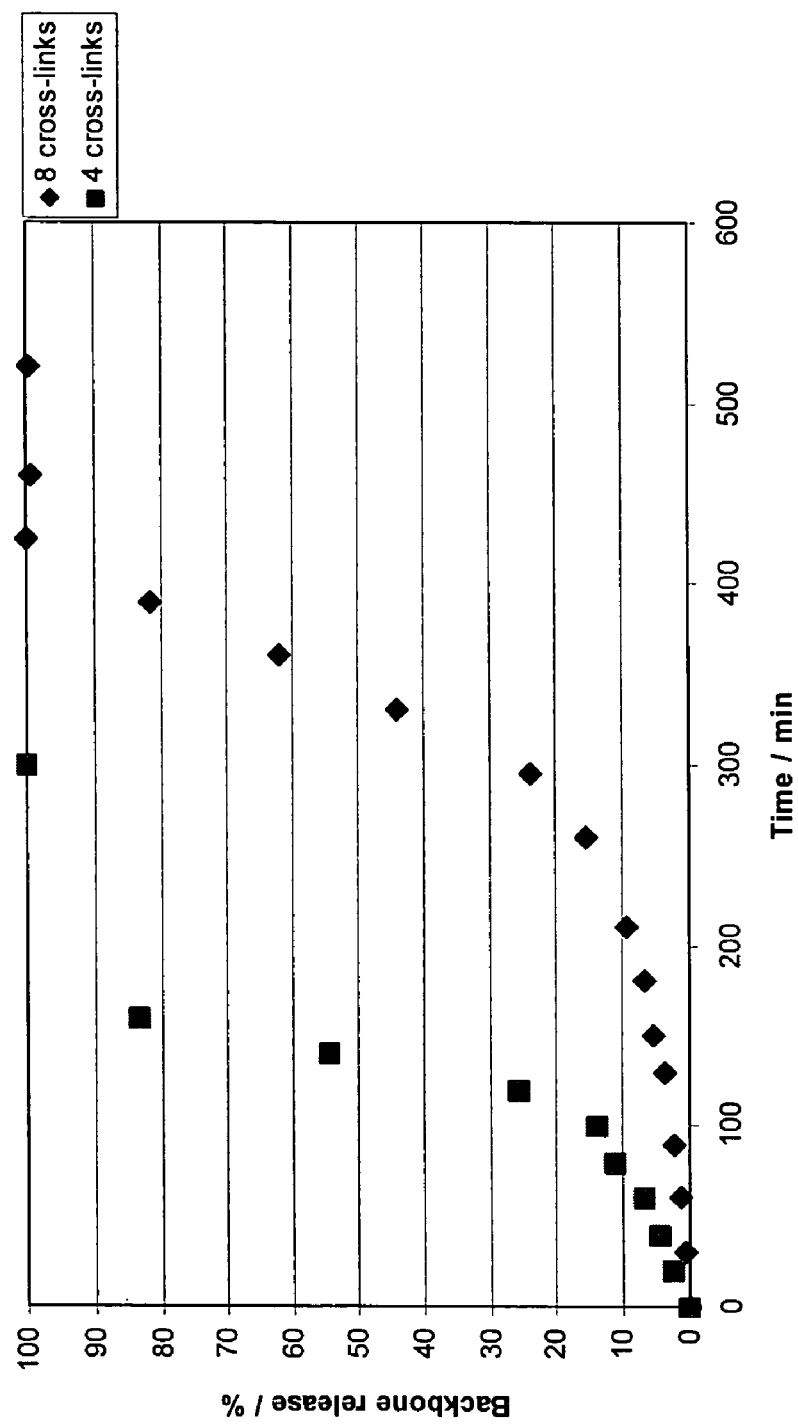
FIG. 10 shows the degradation of biodegradable hydrogels

50 mg of hydrogel 20 or 21 was suspended in 1 ml 50 mM sodium borate buffer (pH 9.0), 150 mM NaCl, 0.005% Tween and incubated at 37° C. 30 µl samples were taken at regular intervals and quantitatively analyzed for polymer backbone coupled naphthyl 22 or 23 by photometry at 280 nm (FIG. 10). The degradation kinetic shows a sigmoidal curve.

ABBREVIATION

Ado 8-amino-3,6-dioxa-octanoyl
Boc t-butyloxycarbonyl
DBU 1,3-diazabicyclo[5.4.0]undecene
DCM dichloromethane
(iv)Dde 1-(4,4-dimethyl-2,6-dioxo-cyclohexyliden)3-methyl-butyl
DIC diisopropylcarbodiimide
DIEA diisopropylethylamine
DMF N,N-dimethylformamide
EDTA ethylenediaminetetraacetic acid
fmoc 9-fluorenylmethoxycarbonyl
Fmoc-Ado-OH Fmoc-8-amino-3,6-dioxaoctanoic acid
HEPES N-(2-hydroxyethyl)piperazine-N'-(2-ethanesulfonic acid)
HOBt N-hydroxybenzotriazole
LCMS mass spectrometry-coupled liquid chromatography
mp 3-maleimidopropionyl
MS mass spectrum
MW molecular mass
PEG poly(ethylene glycol)
RP-HPLC reversed-phase high performance liquid chromatography
RT room temperature
SAMA-OPfp S-acetyl-mercaptoacetic acid pentafluorophenyl ester
SEC size exclusion chromatography
TBTU O-(Benzotriazol-1-yl)-N,N,N',N'-tetramethyluronium tetrafluoroborate
TES triethylsilane
TFA trifluoroacetic acid The various publications, patents, patent applications and published applications mentioned in this application are hereby incorporated by reference herein.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

The invention claimed is:
1. A method for the manufacture of a mesoporous hydrogel-biologically active moiety conjugate, comprising:
   synthesizing the mesoporous hydrogel; and
   after completing all said synthesizing covalently connecting a prodrug linker to the mesoporous hydrogel; and
   conjugating a biologically active moiety to the prodrug linker; wherein the connecting and the conjugating can be carried out in either order.

2. The method of claim 1, wherein the prodrug linker has two functional groups, a first one of the two functional groups being complementary to a functional group attached to the mesoporous hydrogel and a second one of the two functional groups being conjugable to the biologically active moiety.

3. The method of claim 2, wherein the first one of the two functional groups is selected from the group of functional groups consisting of carboxylic acid, amino, maleimide, thiol, sulfonic acid, carbonate, carbamate, hydroxyl, aldehyde, ketone, hydrazine, isocyanate, isothiocyanate, phosphoric acid, phosphonic acid, haloacetyl, alkyl halides, acryloyl, alpha-beta unsaturated michael acceptors, arylating agents, aryl fluorides, hydroxylamine, disulfides, vinyl sulfone, vinyl ketone, diazoalkanes, diazoacetyl compounds, epoxide, oxirane, and aziridine.

4. The method of claim 2, wherein the first one of the two functional groups is selected from the group of functional groups consisting of thiol, maleimide, amino, carboxylic acid, carbonate, carbamate, aldehyde, and haloacetyl.

5. The method of claim 2, wherein the second one of the two functional groups is selected from the group of functional groups consisting of carboxylic acid, carbonate, hydroxyl, hydrazine, hydroxylamine, maleamic acid, ketone, amino, aldehyde, thiol and disulfide groups.

6. The method of claim 2, wherein the biologically active moiety has a moiety functional group complimentary to the second one of the two functional groups.

7. The method of claim 6, wherein the moiety functional group is selected from the group of functional groups consisting of thiol, carboxylic acid, amino, hydroxyl, ketone and imidazole.

8. The method of claim 1, wherein the biologically active moiety is a biopolymer.

9. The method of claim 1, wherein the biologically active moiety is selected from the group of proteins or polypeptides consisting of ACTH, adenosine deaminase, agalsidase, albumin, alfa-1 antitrypsin (AAT), alfa-1 proteinase inhibitor (API), alteplase, anistreplase, ancrod serine protease, antibodies (monoclonal or polyclonal, and fragments or fusions), antithrombin III, antitrypsins, aprotinin, asparaginases, biphalin, bone-morphogenic proteins, calcitonin (salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucocerebrosidase, granulocyte macrophage colony stimulating factor (GM-CSF), phospholipase-activating protein (PLAP), gonadotropin chorionic (hCG), hemoglobins, hepatitis B vaccines, hirudin, hyaluronidases, idurnonidase, immune globulins, influenza vaccines, interleukins (1 alfa, 1 beta, 2, 3, 4, 6, 10, 11, 12), IL-1 receptor antagonist (rhIL-1ra), insulins, interferons (alfa 2a, alfa 2b, alfa 2c, beta 1a, beta 1b, gamma 1a, gamma 1b), keratinocyte growth factor (KGF), transforming growth factors, lactase, leuprolide, levothyroxine, luteinizing hormone, lyme vaccine, natriuretic peptide, pancrelipase, papain, parathyroid hormone, PDGF, pepsin, platelet activating factor acetylhydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urate oxidase, urokinase, vaccines, and plant proteins such as lectins and ricins.

10. The method of claim 1, wherein the biologically active moiety is insulin.

11. The method of claim 1, wherein the hydrogel is functionalized with a functional group selected from the group of reactive functional groups consisting of carboxylic acid, amino, maleimide, thiol, sulfonic acid, carbonate, carbamate, hydroxyl, aldehyde, ketone, hydrazine, isocyanate, isothiocyanate, phosphoric acid, phosphonic acid, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, epoxide, oxirane, and aziridine.

12. The method of claim 1, wherein the hydrogel is functionalized with a functional group selected from the group of functional groups consisting of thiol, maleimide, amino, carboxylic acid, carbonate, carbamate, aldehyde, and haloacetyl.

13. The method of claim 1, wherein the prodrug linker is attached to a non-degradable backbone of the mesoporous hydrogel.

14. The method of claim 13 wherein crosslinkers of the mesoporous hydrogel further comprise biodegradable bonds selected from the group of chemically-cleavable bonds consisting of phosphate, phosphonate, carbonate, carbamate, disulfide and ester bonds.

15. The method of claim 1, wherein the mesoporous hydrogel further comprises biodegradable bonds that are enzymatically cleavable.

16. The method of claim 1, wherein the synthesizing the mesoporous hydrogel comprises a condensation reaction.

* * * * *

UNITED STATES PATENT AND TRADEMARK OFFICE
CERTIFICATE OF CORRECTION

PATENT NO.         : 7,968,085 B2                              Page 1 of 1
APPLICATION NO.    : 10/960851
DATED              : June 28, 2011
INVENTOR(S)        : Ulrich Hersel et al.

It is certified that error appears in the above-identified patent and that said Letters Patent is hereby corrected as shown below:

Column 1, line 2, add: -- CROSS-REFERENCE TO RELATED APPLICATIONS
The priority of United Kingdom Patent Application No. 0415041.3 filed July 5, 2004 and the priority of European Patent Application No. 04019303.9 filed August 13, 2004 are hereby claimed under the provisions of 35 U.S.C. §119. --.

Column 36, lines 45-46: "TBTU O-(Benzotriazol-1-yl)-N,N,N',N'-tetramethyluronium" should be -- TBTU O-(Benzotriazol-1-yl)-N,N,N',N'-tetramethyluronium tetrafluoroborate --.

Column 36, line 47: "tetrafluoroborate" should be deleted.

Signed and Sealed this
Thirteenth Day of September, 2011

David J. Kappos
*Director of the United States Patent and Trademark Office*